United States Patent [19]
Delwiche et al.

[11] Patent Number: 6,001,346
[45] Date of Patent: *Dec. 14, 1999

[54] AQUEOUS EMULSION COMPRISING BIODEGRADABLE CARRIER FOR INSECT PHEROMONES AND METHODS FOR CONTROLLED RELEASE THEREOF

[75] Inventors: Michael Delwiche, Winters; John M. Krochta, Davis; Richard E. Rice, Dinuba, all of Calif.; Cynthia Atterholt, Waynesville, N.C.

[73] Assignee: The Regents of the University of California, Oakland, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/711,159

[22] Filed: Sep. 9, 1996

Related U.S. Application Data

[63] Continuation-in-part of application No. 08/325,040, Oct. 18, 1994, abandoned, which is a continuation-in-part of application No. 08/022,117, Feb. 25, 1993, abandoned.

[51] Int. Cl.$^6$ .......................... A01N 25/02; A01N 25/08; A01N 25/30; A01N 25/00
[52] U.S. Cl. ........................ 424/84; 424/409; 424/417; 424/420; 424/450; 424/484; 71/DIG. 1; 514/785; 514/786; 514/787; 514/789; 514/937; 514/938; 514/939; 514/940; 514/941; 514/942; 514/943; 514/964; 514/970; 514/971; 514/972; 514/973; 514/975
[58] Field of Search ...................... 71/DIG. 1; 514/789, 514/785, 786, 787, 937, 938, 939, 940, 941, 942, 943, 964, 970, 971, 972, 973, 975; 424/DIG. 10, 84, 409, 417, 420, 450, 484

[56] References Cited

U.S. PATENT DOCUMENTS

| | | | |
|---|---|---|---|
| 3,761,584 | 9/1973 | McGovern et al. | 424/84 |
| 3,954,968 | 5/1976 | McKibben | 424/84 |
| 4,042,681 | 8/1977 | Underhill et al. | 424/84 |
| 4,059,689 | 11/1977 | Struble et al. | 424/84 |
| 4,932,994 | 6/1990 | Koester et al. | 71/DIG. 1 |
| 5,002,971 | 3/1991 | Becker et al. | 514/549 |

OTHER PUBLICATIONS

An ASAE Meeting Presentation (Paper No. 94–1597), Dec. 1994.

Proceeding of the 22$^{nd}$ International Symposium on Controlled Release of Bioactive Material, Abstract #2221, 1995.

International Organization for Biological Control International Conference Technology transfer in Biological Control: from research to practice Efficacy of Mating Disruption Pheromones in Paraffin Emulsion Dispenser's, Sep. 1996.

Farm Chemicals Handbook '95, Meister Publishing Co., Ohio, p. C148, 1995.

Chemical Abstracts: 98:102632 (1983).

*Primary Examiner*—John Pak
*Attorney, Agent, or Firm*—Townsend and Townsend and Crew

[57] ABSTRACT

A sprayable or solid biodegradable wax carrier for insect pheromones and a method for constant release rate of the pheromone from the biodegradable wax. A composition comprising a pheromone and paraffin wax formulated as an aqueous emulsion or a solid suitable for application to a surface of a tree or crop for mating disruption of insect pests. Pheromone is released by diffusion or by partitioning from the biodegradable wax carrier or by pheromone exposure due to the biodegradable wax carrier degradation.

37 Claims, 13 Drawing Sheets

6,001,346

AQUEOUS EMULSION COMPRISING BIODEGRADABLE CARRIER FOR INSECT PHEROMONES AND METHODS FOR CONTROLLED RELEASE THEREOF

This is a continuation-in-part application of the patent application Ser. No. 08/325,040 filed Oct. 18, 1994, now abandoned, which is a continuation-in-part application of the patent application Ser. No. 08/022,117 filed on Feb. 25, 1993, abandoned.

BACKGROUND OF THE INVENTION

1. Field of the Invention

This invention concerns a sprayable or solid biodegradable wax carrier for insect pheromones and a method for a constant-rate and continuous release of pheromones from the carrier. In particular, the invention concerns a composition comprising the pheromone formulated in a paraffin wax carrier. The composition is formulated as an aqueous paraffin emulsion or as paraffin wax granules or solids. The composition is useful for mating disruption of insect pests and dispensing other bioactive compounds.

2. Background and Related Art

In recent years there has been an increased awareness and interest in biological control of insect pests as an alternative to the use of chemical pesticides (*Biological Approaches to Pest Management in California*, ANR Publication 21512, University of California, Oakland, Calif., 1992). Reasons for this interest include insect resistance to traditional pesticides, public concern for the environment, food safety, and worker health. Also, while fewer new pesticides are being introduced to the market due to registration and research costs, other pesticides are being withdrawn from the market because of environmental and health concerns. This has placed farmers in the difficult position of trying to grow crops without jeopardizing yield and crop quality on one side, or environmental safety and worker health on the other side.

One method of biological control which has proven successful is the use of synthetic insect sex pheromones for pest control by mating disruption. Since much of an insect's behavior is chemically controlled, there is an opportunity to interfere with the natural chemical communication between insects as a means of controlling insect pests. (*Behavior-modifying Chemicals for Insect Management, Applications of Pheromones and Other Attractants*, Vol. I, R. L. Ridgway, et al, Eds., Marcel Dekker, Inc., New York, N.Y. 1990).

Pheromones are semio-chemicals, that is behavior-modifying chemicals, that act as signals to other insects of the same species. Over 1600 pheromones have been identified to date, and many of these compounds can be synthetically produced (*Semio-Chemicals in Crop Protection*, PJB Publications Ltd., New York, N.Y., 1992). Typically, for mating disruption, a small amount of pheromone is released from a dispenser or carrier material at a level above the concentration released by female insects. When the background level of synthetic pheromone released is above a threshold, male insects are unable to locate female insects. The male's inability to find a mate will then control future populations of the insect pest (*Insect Suppression with Controlled Release Pheromone Systems*, Vol. I, 3–12, Kydonieus, A. et al, Eds, CRC Press, Inc., Boca Raton, Fla., 1982).

Insect control with pheromones requires a controlled release of the target pest's sex pheromone at the appropriate time, location, and concentration to prevent males from chemically locating and mating with fertile females, and thus control future generations. In order to make mating disruption with pheromones competitive with conventional methods of insect control, efficient means of application as well as dispensing systems that release the pheromones in a constant-rate and continuous manner throughout the field or orchard are needed.

One limitation for the widespread use of mating disruption as a pest control has been a lack of a sprayable controlled-release formulation able to release pheromone over an extended period of time of at least six weeks but preferably for one crop cycle or season.

Currently available commercial pheromone dispensers are made from plastic, are not biodegradable, and must be manually placed on trees. Sprayable pheromone materials that can be applied to field crops are typically synthetic microcapsules that release the pheromone over a relatively short period of time and are difficult to stick to plant surfaces.

Attempts to provide slow release dispensers for pheromones led to development of pheromone dispensers such as microcapsules, trilaminates, capillaries, "ropes" and liquid-flowables. These dispensers release the pheromone by either evaporation from capillaries or ropes (hollow tubes), by diffusion through a polymeric dispenser, or by diffusion through a microcapsule wall.

The main disadvantages of the above described dispensers are a necessity for manual placement of traps, limitation on the dispensers application height to due workers standing on ground, and their nonbiodegradability.

Another factor that has limited the development of a satisfactory sprayable material is the need for continuous and constant-rate (i.e., zero-order) pheromone release which is needed in order to maintain a constant pheromone release above the threshold necessary for mating disruption. To date, a formulation providing such continuous and constant-rate release over the extended periods of insect mating seasons has not been described.

Thus, there is a need for a sprayable carrier that allows continuous constant-rate release of the pheromone over extended time periods.

A problem encountered with all the above-listed methods and dispensers for delivery of pheromone is the inability to provide microcapsules or formulations which adhere to the treated surfaces, and which allow constant, continuous and controllable release-rate over 2 to 6 month periods.

It would, therefore, be advantageous to provide a carrier for the delivery of the pheromone to the treated surface and allow and assure the pheromone's release in a predetermined continuous and constant-rate during mating periods.

It is, therefore, a primary objective of this invention to develop a sprayable or solid biodegradable carrier material which will release pheromones over extended periods of time and disrupt insect mating.

All patents, patent applications and publications cited herein are hereby incorporated by reference.

SUMMARY

One aspect of this invention is a biodegradable wax carrier for insect pheromones selected from the group consisting of paraffin, beeswax, carnauba wax, lanolin, shellac wax, bayberry wax, sugar cane wax, microcrystalline, ozocerite, ceresin, montan, candelilla wax, and a combination thereof.

Another aspect of this invention is a biodegradable wax carrier for insect pheromones alone, for bioactive agents alone, or in combination with the pheromone.

Another aspect of this invention is a biodegradable wax carrier in admixture with one or more additives to adjust the release rate, suitable for formulation of insect pheromones alone, other bioactive compounds alone or in combination with the pheromones.

Another aspect of this invention is a biodegradable paraffin wax carrier for insect pheromones which is sprayable, squirtable, spreadable or solid.

Another aspect of this invention is an aqueous emulsion comprising a pheromone dispersed in a paraffin wax from which the pheromone is released continuously at a constant rate.

Another aspect of this invention is a solid paraffin wax in form of solid blocks or granules comprising a dispersed pheromone from which the pheromone is released continuously at a constant rate.

Still yet another aspect of this invention is a composition comprising a biodegradable paraffin wax and a pheromone suitable for control of insect mating from which the pheromone is continuously released by diffusion, by partitioning, or by exposure of the pheromone upon the paraffin degradation.

Another aspect of this invention is a method for a constant, continuous and controlled release of a pheromone from a biodegradable paraffin wax carrier.

Still yet another aspect of this invention is a method for disrupting insect mating, said method comprising steps:

(a) formulating a composition of a pheromone in a biodegradable paraffin wax;

(b) applying the composition from which the pheromone is released at a continuous and constant-rate to a surface to be treated.

Still yet another aspect of the current invention is a method for disrupting insect mating by spraying, squirting, spreading or placing a biodegradable paraffin wax and an insect pheromone, on the surface to be treated.

DEFINITIONS

Figure 1:
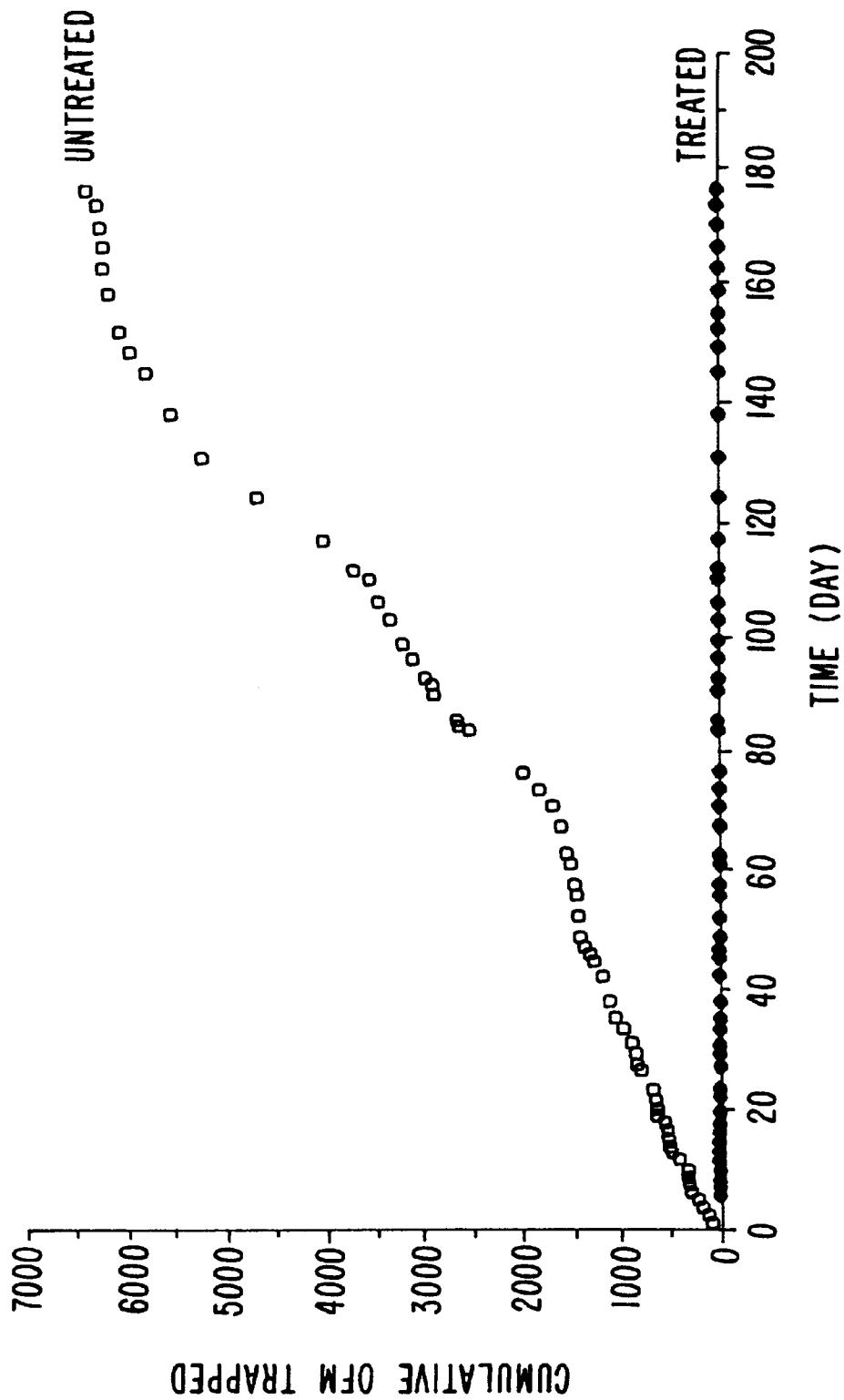
FIG. 1 is a graph showing the number of oriental fruit moths caught in four traps at the center of each block treated with pheromone formulated in solid paraffin and four traps in untreated blocks of a commercial almond orchard.

As used herein:

"Biodegradable carrier", "biomaterial" or "carrier" means a biodegradable wax, such as beeswax, lanolin, shellac wax, carnauba wax, fruit wax (such as bayberry or sugar cane wax), candelilla wax, paraffin, and other waxes such as microcrystalline, ozocerite, ceresin, montan, or their combination. The biodegradable carriers formulated according to the invention allow a zero-order, constant-rate, linear, continuous, sustained and controlled release rate of the pheromone and bioactive compounds. The term carrier includes biomaterials formulated and/or applied as sprayable aqueous solutions, or as solids, such as paraffin blocks or granules.

"Wax" means a low melting organic mixture or compound of high molecular weight, solid at room temperature.

"Pheromones" means behavior-modifying chemicals, also called semio-chemicals that act as signals to other insects of the same species. Typically and for the purposes of this invention, a pheromone means any substance released by one sex (i.e., female) insect species which influences the behavior of the opposite sex (i.e., male) insect of the same species. In this capacity, the pheromone is capable of disrupting mating or otherwise controlling the insect population.

"Bioactive compound" means a compound such as a lure, pesticide, fungicide, herbicide, micronutrient, bacterium (such as *Bacillus thuringiensis*), insect pathogenic virus (such as celery looper virus), fertilizer, plant mineral supplement, or other bio-control agent which can be added to the emulsion to meet specific needs of crop production.

"Coating" means a surface cover of a carrier formulation containing a pheromone, sprayed on a treated surface. "OFM" means oriental fruit moth, *Grapholita molesta* (Busck) (Lepidoptera).

"Composition" means a formulation comprised of a mixture of a biodegradable wax carrier and a pheromone. The composition may optionally contain selected additives or other bioactive compounds.

"Additive" means a compound added to the formulation which either enables adjustment of the pheromone release rate or affects the physical properties of the mixture. Examples of additives are listed in Section III.

"Microencapsulated" or "entrapped" means physically and/or chemically holding a pheromone or a bioactive agent within the carrier material.

"Spraying" means applying an aqueous emulsion of a biodegradable wax carrier containing the bioactive agent by spraying, squirting, splatting, or applying as a granular material to a treated surface.

"Zero-order release rate" means the constant release rate of the pheromone from the biodegradable carrier. The plot of mass of pheromone released vs. time is linear.

"First-order release rate" means the release rate which is a function of and depends on the amount of a dispersed residual pheromone within a wax carrier.

"Air/wax partition coefficient" means the equilibrium concentration of the pheromone or other bioactive agent in the air divided by the concentration of the bioactive agent in the carrier wax. As the solubility of the pheromone in the carrier material increases, the partition coefficient decreases and the release-rate also decreases.

DETAILED DESCRIPTION OF THE INVENTION

The current invention provides a composition and a method for continuous and constant-rate release of a pheromone from a wax carrier. A composition comprises an insect pheromone formulated in a sprayable aqueous emulsion or in a solid biodegradable wax carrier. A method provides a continuous and constant release rate of the pheromone from the carrier. The release-rate is adjustable and controllable by optional addition of one or more additives to the wax carrier. Plant growth and protection are enhanced by optional addition of other bioactive agents.

Briefly, the composition of the invention either in the sprayable or solid form is applied directly to or on the treated areas or surfaces, such as orchards, gardens, plants, trees or soil. The sprayable composition quickly forms a coating on the treated surface from which the pheromone, providing protection of a crop from the insect infestation, is released in a continuous, constant-rate, zero-order and controlled manner. Alternatively, the formulation is applied as a solid composition, such as granules or disks, releasing the pheromone at a continuous and constant-rate from the solid wax.

The method of the invention allows longer and more efficient insect control by providing a more constant release rate of the pheromone from the wax carrier than any other method known previously.

Using a variety of additives for control of the release rate from the carrier wax, the formulation can be custom designed. The amount of the pheromone is calculated to be sufficient to provide insect control during the mating season (s) and for the whole time when such protection is needed. Unless otherwise specifically stated, amounts of all components are in % weight.

The release rate of the pheromone from the biodegradable carrier is controlled by selection of the biodegradable wax carrier, by the respective concentrations of the biodegradable carrier and the pheromone and their ratios, by the physical properties and characteristics of the carrier/pheromone composition, by the presence or absence of the additive, by the additive's type and concentration, by a formulation, by the application conditions, by the weather and by the season. For example, the thickness of the coating layer is critical for the release-rate such that a slower release-rate is achieved when such composition is applied as a thicker coating, from thicker paraffin disks or from bigger granules. Conversely, a faster release-rate is achieved with compositions containing only a wax carrier without additives, having larger concentrations of the pheromone and applied as thin coatings, larger area disks, or smaller granules.

The release rate of the pheromone is affected by the presence of additives, such as antioxidants and/or volatility suppressants incorporated into the wax carrier together with pheromone. Volatility suppressants decrease the release-rate of the pheromone. Antioxidants such as vitamin E increase the stability of the pheromone and slow its degradation and oxidation. Consequently, the composition containing these additives is more economical and has an improved longevity over the one where the pheromone is unprotected and may be subjected to oxidation.

The invention is versatile in that the employed variables allow preparation of compositions having a slow or fast release of large or small amounts of pheromone at a continuous and constant release rate during the predetermined time.

All the above-listed parameters are variable and their variation provides compositions having different release rates of pheromone. All variations of these properties are intended to be within the scope of the invention.

I. Bioactive Agents a. Pheromones—Primary Bioactive Agents

The primary bioactive agents of this invention are pheromones, compounds which affect insect mating and reproduction and include pheromones of all insect species. The species-specific insect pheromones disrupt mating or otherwise affect reproduction and control populations of the insect pests. Pheromones may be added singly or two or more pheromones may be formulated together in one carrier formulation. Pheromones are added in amounts from about 0.0001 to about 10%, by weight.

b. Secondary Bioactive Agents

Secondary bioactive agents are selected from the group of compounds such as lures, juvenile hormones, plant hormones, pesticides, fungicides, herbicides, nutrients and micronutrients, bacteria (such as *Bacillus thuringiensis*), insect pathogenic viruses (such as celery looper virus), fertilizers, plant mineral supplements, and other biocontrol agents which can be added to meet specific needs of the grower. Secondary bioactive agents are added in amounts from about 0.0001% to about 10% preferably between about 1–5%, by weight.

Both primary and secondary bioactive agents may be formulated individually or in combination with one another, depending on the intended use. For example, if the orchard is infested with more than one insect, one or more species-specific pheromones for these insects may be formulated together in one composition. If the orchard is additionally infested with other insect pests, the pheromone may be formulated, for example, together with the insect pathogenic virus or with the other bioactive agents.

II. Biodegradable Carriers

Biodegradable carriers of the invention are compounds able to form an aqueous sprayable emulsion or solid block or granules. After spraying, the aqueous emulsion will dry to form a coating containing pheromone. Pheromone is then continuously released from the coating, solid block or granules under controlled conditions.

The biodegradable carriers of this invention are waxes, such as beeswax, lanolin, shellac wax, carnauba wax, fruit wax (such as bayberry or sugar cane wax) candelilla wax, other waxes such as microcrystalline, ozocerite, ceresin, montan or, preferably, paraffin used in amounts from 10–100%, by weight.

Paraffin, which is easy to handle, has a practical melting point and is relatively inexpensive, is the most preferred carrier for formulating a variety of pheromones and other bioactive agents.

Paraffin has a melting point in the range of 50–60° C. (120–140° F.), is nonpolar and miscible with pheromone when molten. Paraffin has now been found to provide continuous and constant release-rates for the pheromone in the ranges desired for insect mating disruption. Paraffin can be applied at field temperatures as an aqueous emulsion which adheres to plant bark or foliage, releases pheromone for an extended period of time, slowly erodes from plant surfaces and biodegrades in the soil. Alternatively, paraffin/pheromone dispersion can be formulated as solids or granules.

For formulation of the pheromone, the paraffin wax may be used alone or in combination with other types of biodegradable carriers, or in combination with a variety of additives, listed below.

III. Additives

A variety of additives may be incorporated into compositions of the biodegradable wax carriers and pheromones. These additives typically change and/or enhance the physical characteristics of the carrier material and are, therefore, suitable for designing compositions having specific requirements as to the release rate and amount of the released pheromone, protection of the wax composition against destruction by weather conditions, etc. These additives are, among others, plasticizers, volatility suppressants, antioxidants, lipids, various ultraviolet blockers and absorbers, or antimicrobials, added in amounts from about 0.001% to about 10%, preferably between 1–6%, by weight.

Antioxidants, such as vitamin E, BHA (butylated hydroxyanisole), BHT (butylated hydroxytoluene), and other antioxidants which protect the bioactive agent from degradation, are added in amounts from about 0.1% to about 3%, by weight.

Ultraviolet blockers, such as beta-carotene or p-aminobenzoic acid protect the bioactive agents from light degradation added in amounts from about 1% to about 3%, by weight.

Antimicrobials, such as potassium sorbate, nitrates, nitrites, and propylene oxide, protect the bioactive agents from microbial destruction are added in amounts from 0.1% to about 2%, by weight.

Emulsifiers, such as lecithin and modified lecithins, mono- and diglycerides, sorbitan monopalmitate, sorbitan monooleate, sorbitan monolaurate, polyoxyethylene-sorbitan monooleate, fatty acids, lipids, etc. provide or improve emulsification properties of the composition and are added in amounts from about 1% to about 6%, by weight.

Plasticizers, such as glycerin or soy oil affect physical properties of the composition and may extend its resistance to environmental destruction.

IV. Formulation of the Composition

The composition of the invention is typically formulated by mixing the biodegradable wax, i.e. paraffin, in amounts from about 10% to about 100%, preferably about 30–40%, depending on the type of the wax and on the desired properties of the coating, with from about 50% to about 90% of water, preferably about 60% of water and the pheromone is added in an amount from about 0.01% to about 20%, preferably about 0.1% to about 10%, most preferably about 4%. Additives or other bioactive agents may be optionally added in amounts from about 0.001% to about 20%, preferably in an amount from about 1% to about 10%, depending on the additive or the bioactive agent. The ratio of the carrier wax/water/pheromone/additive/bioactive agent depends on the intended properties of the composition and on the application method.

To formulate the composition, the wax is first heated, under constant stirring, to the melting point temperature typically from about 40° C. to about 80° C., preferably from about 50° C. to about 60° C., depending on the type of the wax. The pheromone and optionally additives or other bioactive agents, alone or in combination, are added directly to the molten wax carrier and the mixture is stirred. Additional water, or emulsifiers, if needed for emulsification, are added to form the final composition. The composition may be stirred or emulsified mechanically. The composition is then cooled and stored as an aqueous emulsion, or the wax is molded into disk dispensers or formulated as granules.

On contact of the emulsion with the treated surface, the water from the applied emulsion evaporates and forms the coating containing the pheromone evenly distributed within. The pheromone is released from the matrix either by diffusing to the surface of the solid where it evaporates, or by degradation or erosion of the matrix.

A biodegradable carrier of this invention alone with or without additives or bioactive agent is also intended to be within a scope of the invention.

V. Testing Methods and Studies

This invention is based on a finding that the biodegradable material affects the release of pheromones. Various biodegradable materials selected from a general group of waxes, or their combination, have been examined. Furthermore, various additives have been incorporated in the biodegradable carriers' formulation to test their effects on the physical characteristics of the coating.

The overall aim of these studies leading to the development of this invention was to design a sprayable biodegradable carrier for release of pheromones having constant and continuous controlled (zero-order) release rate. Carriers or devices with such zero-order release rate use the pheromone most effectively during extended time. Pheromones dispersed in the biodegradable carrier material which are sprayable or squirtable on the tree bark and foliage provide such continuous and constant release rate.

Typically, when the active agent is dispersed in a carrier material, first-order release rate occurs, with the release-rate being a function of the residual active agent leading to decreasing release rates over time. However, in the current invention, when the pheromone was formulated in paraffin according to the invention, zero-order release was obtained. These results show that diffusion of the pheromone through the paraffin matrix is not the rate-controlling mechanism, but rather the partitioning of the pheromone between the wax and the air.

As described in *J. Pharm. Sci.* 63:4 (515) (1974), in a partition-controlled drug release mechanism, the drug being released has a high solubility in the polymeric delivery device and a low partition coefficient between the polymer and the surrounding medium. If the partition coefficient is below a threshold value, the partitioning of the drug to the surrounding medium controls the release-rate, not the diffusion through the polymer, thus giving zero-order release kinetics.

For all described studies oriental fruit moth (OFM) was used as a model pheromone.

In the laboratory, pheromone release-rate was measured by two different methods:

(1) extracting the residual pheromone from coatings aged for different periods of time, and (2) capturing the released pheromone from an air stream passing over the coatings.

In the second method described in Example 3, the release-rate was determined by capturing the pheromone released from a coating into an air stream passing over the coating. A flow cell environmental chamber was designed and built for this purpose. With this controlled environment chamber, the air temperature, humidity, and flow can be varied independently to determine the effect on the release rate of the pheromone.

A number of experiments were performed to determine the stability of the pheromone in the carrier and the stability of the pheromone to oxidation and ultraviolet (UV) degradation.

Field testing has focused on determining phytotoxic effects of the carrier material on orchard trees and evaluations of mating disruption with oriental fruit moth (OFM) pheromone.

Field tests performed during the spring and summer seasons measured the effectiveness of paraffin as a carrier for OFM pheromone. Paraffin disks (7.6 cm diameter) containing 650 mg OFM pheromone and 1.3 g vitamin E were placed in almond trees in 4 different 5-tree groupings. A pheromone sticky trap (Pherocon 1C, Trece, Salinas, Calif.) was placed in the center tree of each grouping to measure the effect of the pheromone treatment on mating behavior. As a control, 4 traps were placed in an untreated area of the almond orchard. The number of insects caught in the traps was counted periodically. In other field trials, emulsions of paraffin/pheromone were applied to sections of a peach orchard and the traps for insects were placed in each treated and untreated area. Results were compared to commercially available pesticide treatments, as seen in Table 1.

Figure 2:
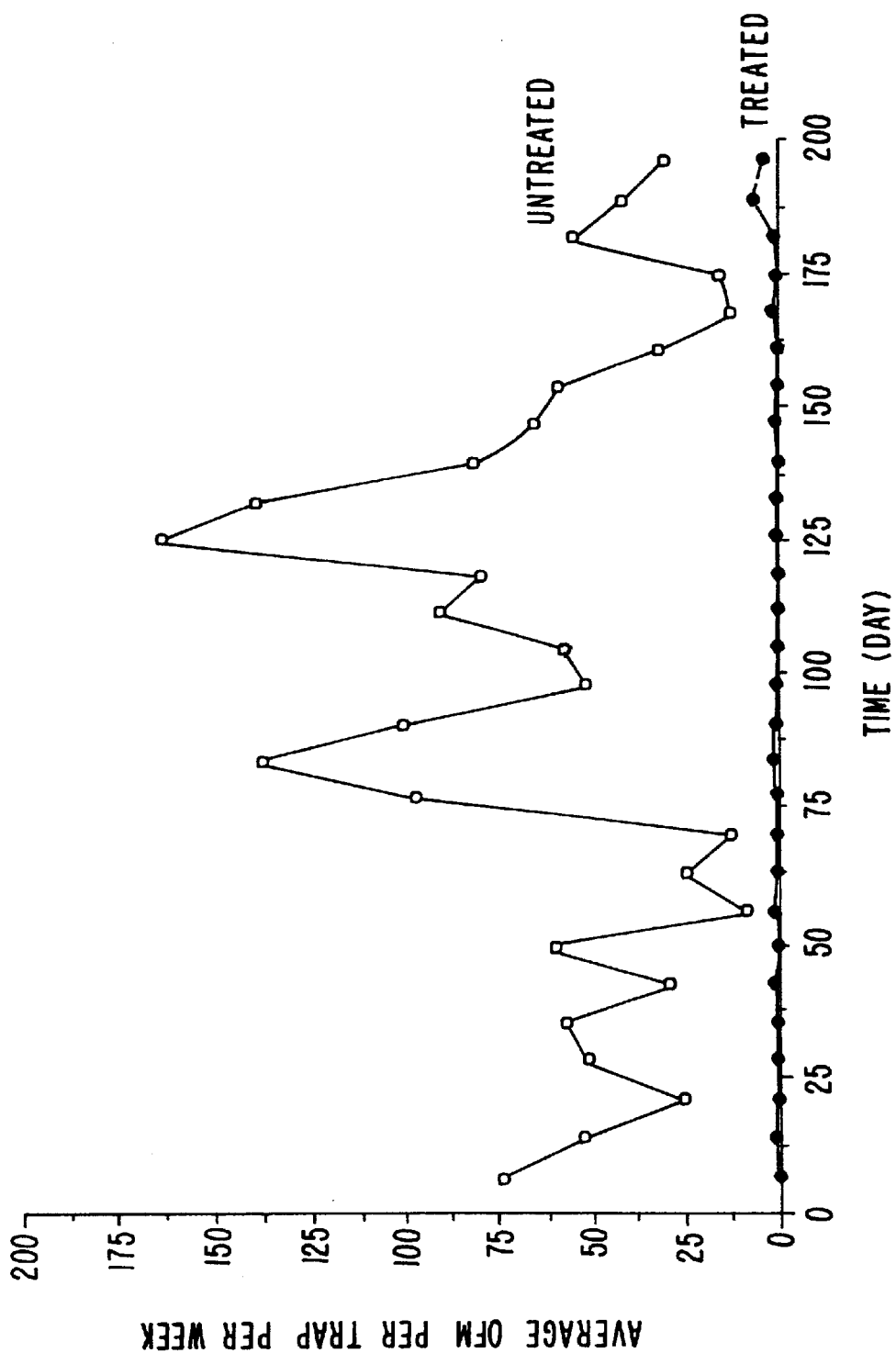
FIG. 2 is a graph showing the average number of oriental fruit moths caught per trap per week in untreated areas and areas treated with pheromone in solid paraffin formulation.
Figure 3:
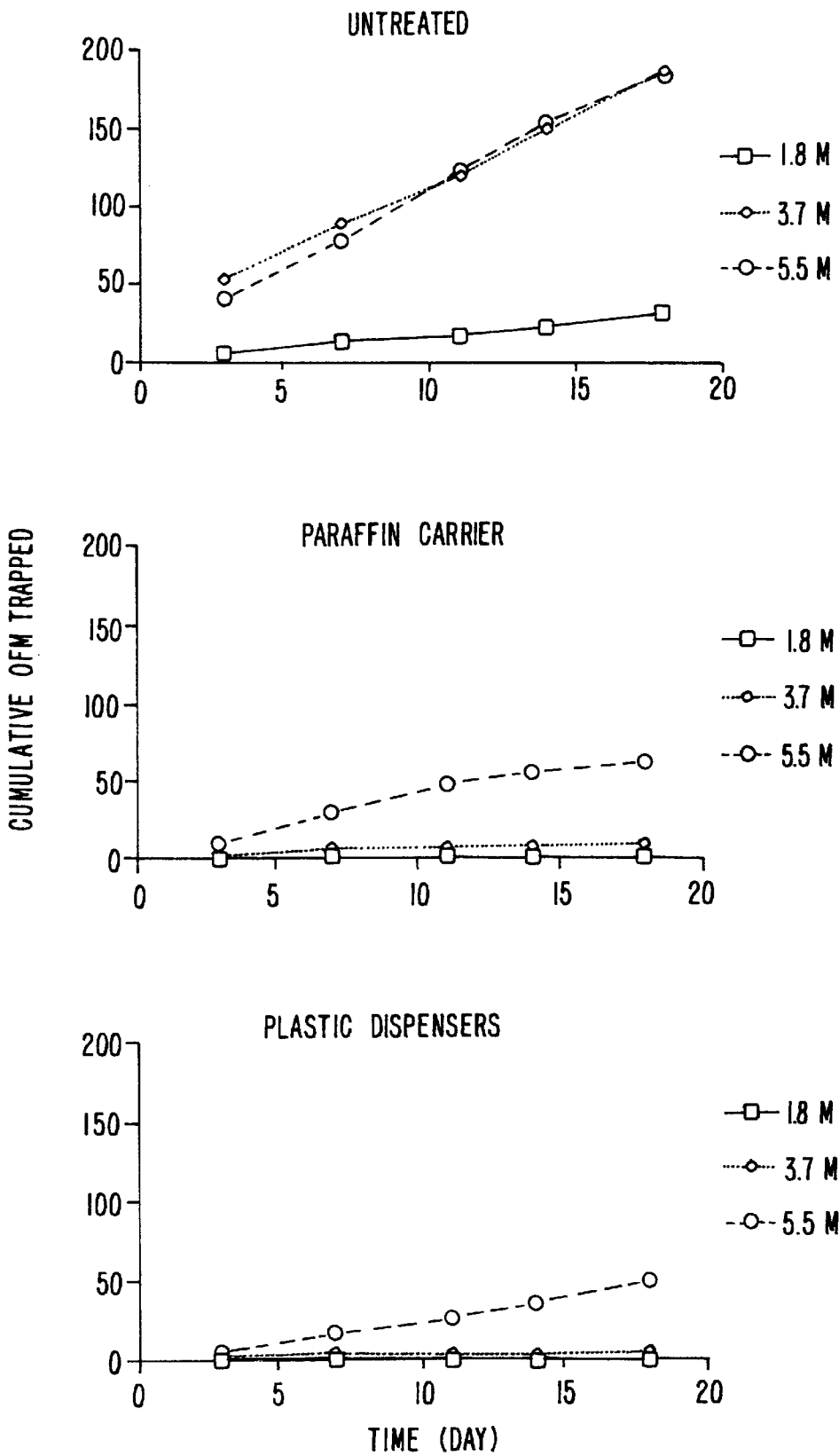
FIG. 3 is shows a cumulative number of oriental fruit moths caught in traps placed in untreated areas, and in the areas treated with a solid paraffin carrier or with plastic dispensers.

Results of both the laboratory and the field tests are seen in FIGS. 1–3.

FIGS. 1 and 2 show the field test results obtained with treatment, according to the invention, of a commercial almond orchard divided into treated and untreated blocks. The data represents the number of OFM caught in 4 traps in an untreated block and 4 traps at the center of each treated block.

FIG. 1 shows the cumulative OFM that were counted in the 4 traps placed in both the treated and untreated blocks. For a period of approximately 6 months, over 6,400 moths were caught in the untreated trees, whereas only 33 moths were caught in the treated trees. The amount of OFM pheromone released from the 15 g paraffin disks containing 650 mg pheromone was sufficient to essentially achieve trap shut-down for the entire season.

FIG. 2 shows the results of the same experiment on an average weekly basis. The fluctuations reflect the different OFM generations and weather effects.

FIG. 3 shows the results of the experiment to measure the vertical distribution of pheromone released from paraffin and commercial plastic dispensers placed in almond trees (at heights of 6, 12 and 18 ft.). Each point shown represents the average of 3 traps. At 6 and 12 ft, almost complete trap shut-down was obtained for both pheromone treatments. Although there were more moths caught at 18 ft, there was still a large difference between the treated and untreated trees. The pheromone wax placed at a height of 6 ft for mating disruption appeared to be diffusing throughout the tree canopy, as evidenced by the OFM trap counts at all 3 heights in the trees.

FIG. 3 shows that there was very little difference between the results obtained with the commercial pheromone dispensers and the pheromone/paraffin disks. Both pheromone dispensing systems worked well at 6 and 12 ft. Both dispensing systems lowered the number of moths trapped in the top part of the tree canopy (18 ft), although this decrease may not be sufficient to reduce crop damage.

Figure 4:
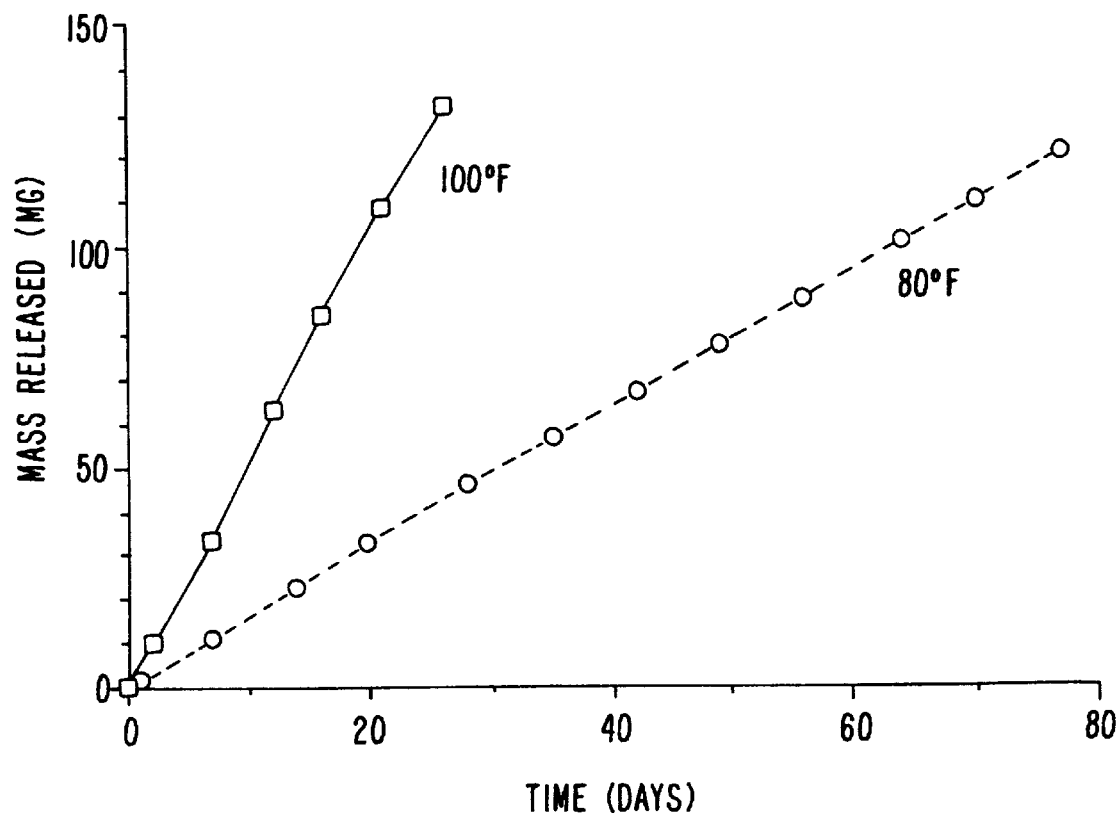
FIG. 4 is a graph illustrating the effect of temperature on oriental fruit moth pheromone release from paraffin emulsions under laboratory conditions.
Figure 5:
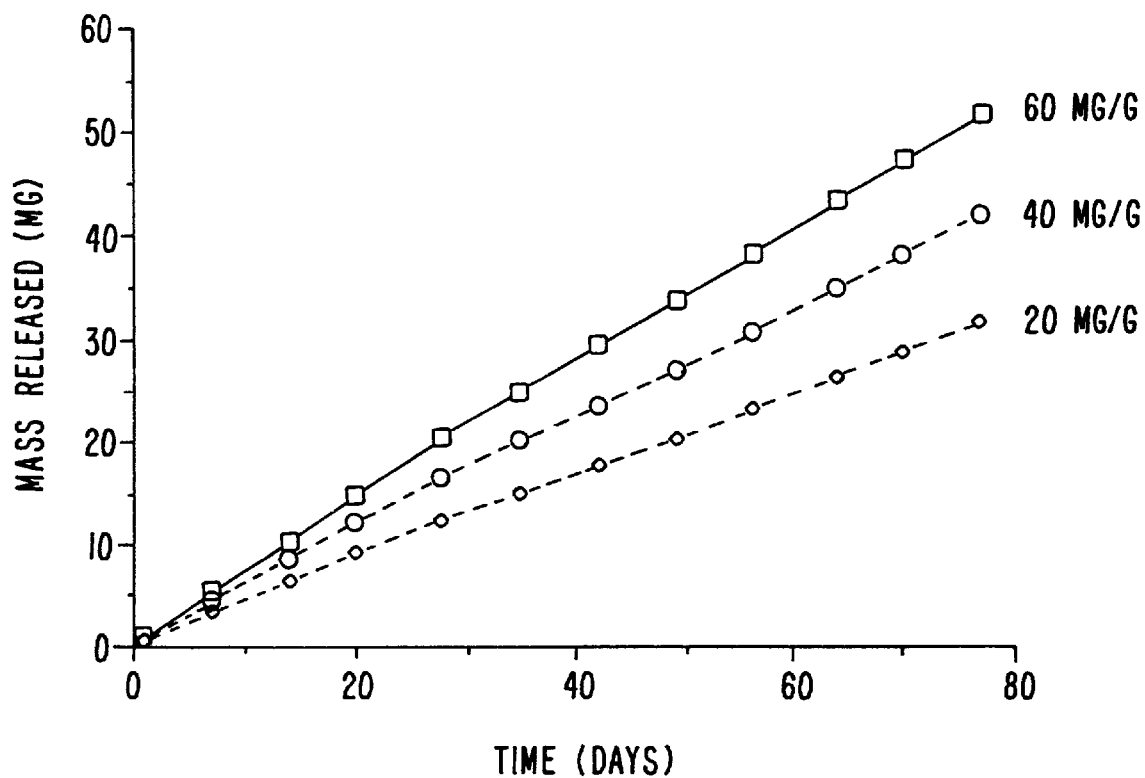
FIG. 5 is a graph illustrating the effect of concentration of oriental fruit moth pheromone on its release from paraffin emulsions.
Figure 6:
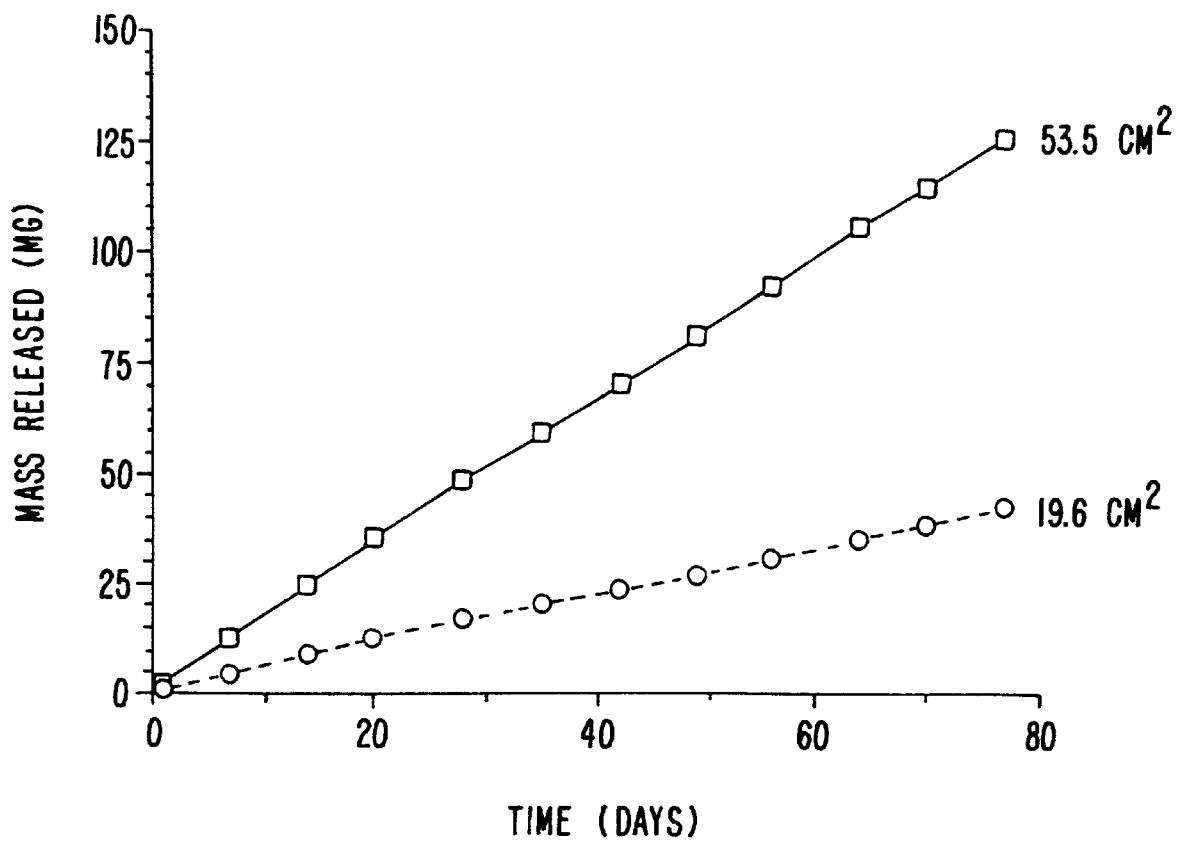
FIG. 6 is a graph illustrating the effect of surface area on oriental fruit moth pheromone release from paraffin emulsions under laboratory conditions.

The results of the lab flow cell experiments performed to measure pheromone release from paraffin emulsions are shown in FIGS. 4–6. These figures show the cumulative amount of pheromone released over time. Five grams of paraffin emulsion were weighed into each flow cell and the emulsion was dried before the flow cells were sealed and placed in the oven. Each of these experiments was replicated three times, and the graphs are averages of these three separate flow cell measurements. The most important finding of these studies is the nearly linear (zero-order) release that was obtained (i.e., constant release rate).

FIG. 4 shows the effect of temperature on the pheromone release rate measured as cumulative OFM released from paraffin emulsions in laboratory flow cells. In this study the pheromone concentration (60 mg/g wet emulsion) and surface area (19.6 $cm^2$) were kept constant while temperature was varied. The experiments were run at 80 and 100° F. to simulate typical summer orchard temperatures. As seen in FIG. 4, when the temperature was increased from 80 to 100° F., there was a three-fold increase in release rate. An exponential effect of temperature on release rate was observed.

The results of an experiment testing the effect of the pheromone concentration on release rate measured as a cumulative release of OFM pheromone from paraffin emulsions are shown in FIG. 5. In this study, the temperature (80° F.) and surface area (19.6 $cm^2$) were kept constant while pheromone concentration was varied. The pheromone concentrations in the paraffin emulsions were 20, 40, and 60 milligrams pheromone per gram wet emulsion. As seen in FIG. 5, the release of the pheromone is linear and constant, and a larger release rate is obtained with a higher pheromone concentration in the paraffin wax matrix, which provides a greater driving force.

FIG. 6 shows the effect of surface area on OFM pheromone release rate from paraffin emulsions in laboratory flow cells. In this experiment, the pheromone concentration and temperature were kept constant, while surface area was varied. The pheromone concentration in the paraffin emulsions was 40 mg pheromone per gram/wet emulsion, and the temperature was kept at 80° F. The results seen in FIG. 6 indicate that there is a linear relationship between exposed surface area and release rate. Thus, the manner in which the material is applied to trees plays a crucial role in release rate. A less viscous emulsion, covering a larger surface area, has a higher release rate, while a more viscous emulsion has a lower release rate and this continues releasing pheromone for a longer period of time.

Figure 7:
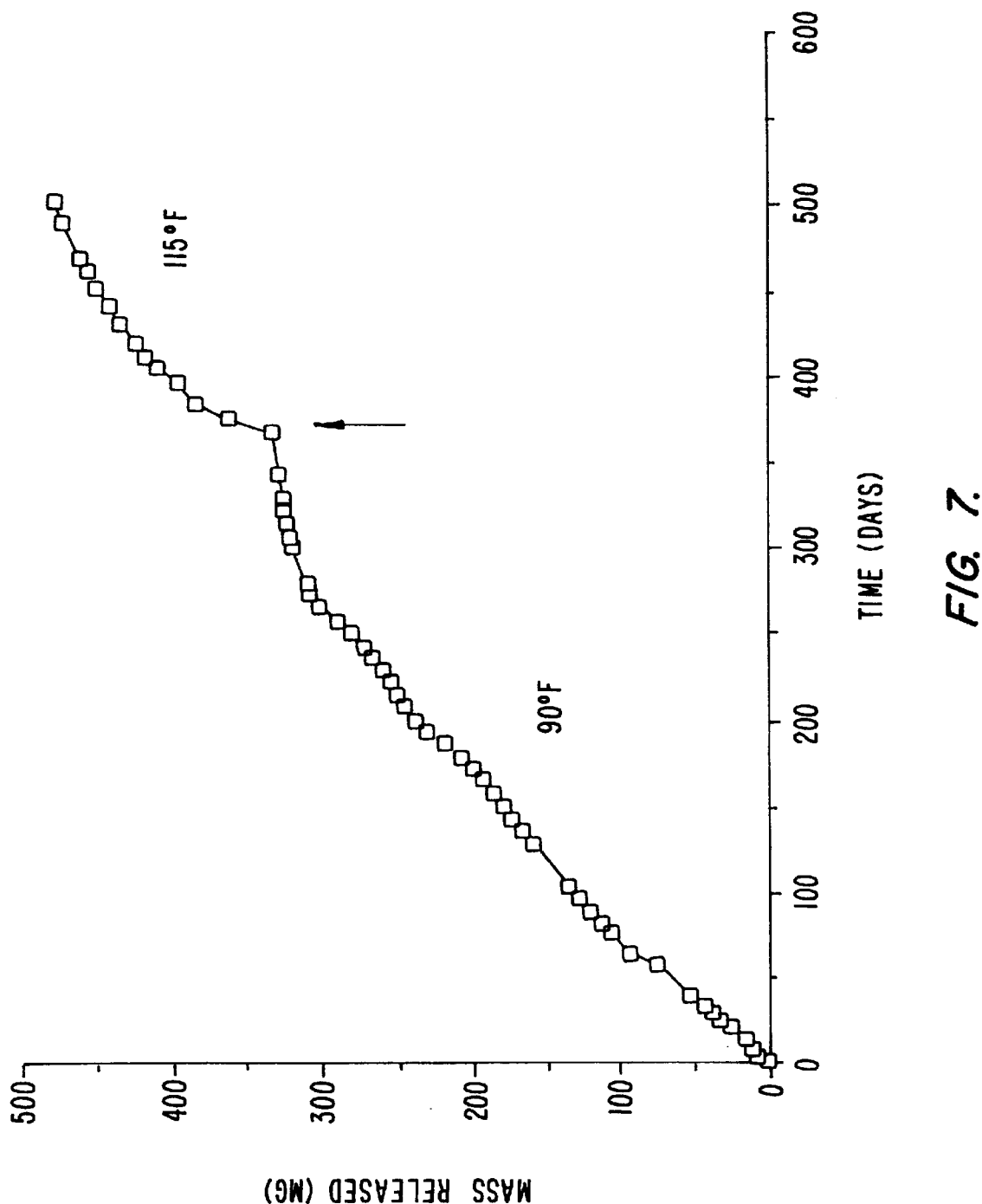
FIG. 7 is a graph illustrating cumulative release of pheromone from a solid paraffin disk for more than 500 days.

The results of a long term study measuring pheromone release from a solid paraffin disk are shown in FIG. 7. The graph shows the cumulative amount of OFM pheromone released over time (500 days) from the flow cell. The paraffin disk had a wax mass of 15 g, a surface area of 45.6 $cm^2$, and contained 650 mg OFM pheromone and 1.3 g vitamin E. For the first year, the temperature was maintained at 90° F. Linear (zero-rate) release was obtained during the first 280 days. At that time approximately 50% of the pheromone had been released. After that, the release rate began to decrease. To measure the amount of pheromone remaining in the paraffin disk, the temperature was then increased to 115° F.

As shown in the graph, the release-rate increased when the temperature was increased, but with the temperature increase, zero-order release stopped and first-order release was obtained instead. To date, approximately 80% of the pheromone added to the paraffin in this experiment has been released. These results confirm that long term pheromone release can be obtained from paraffin.

The results of lab experiments measuring the equilibrium headspace concentration of OFM pheromone in sealed vials are shown in FIGS. 8 to 11.

Figure 8:
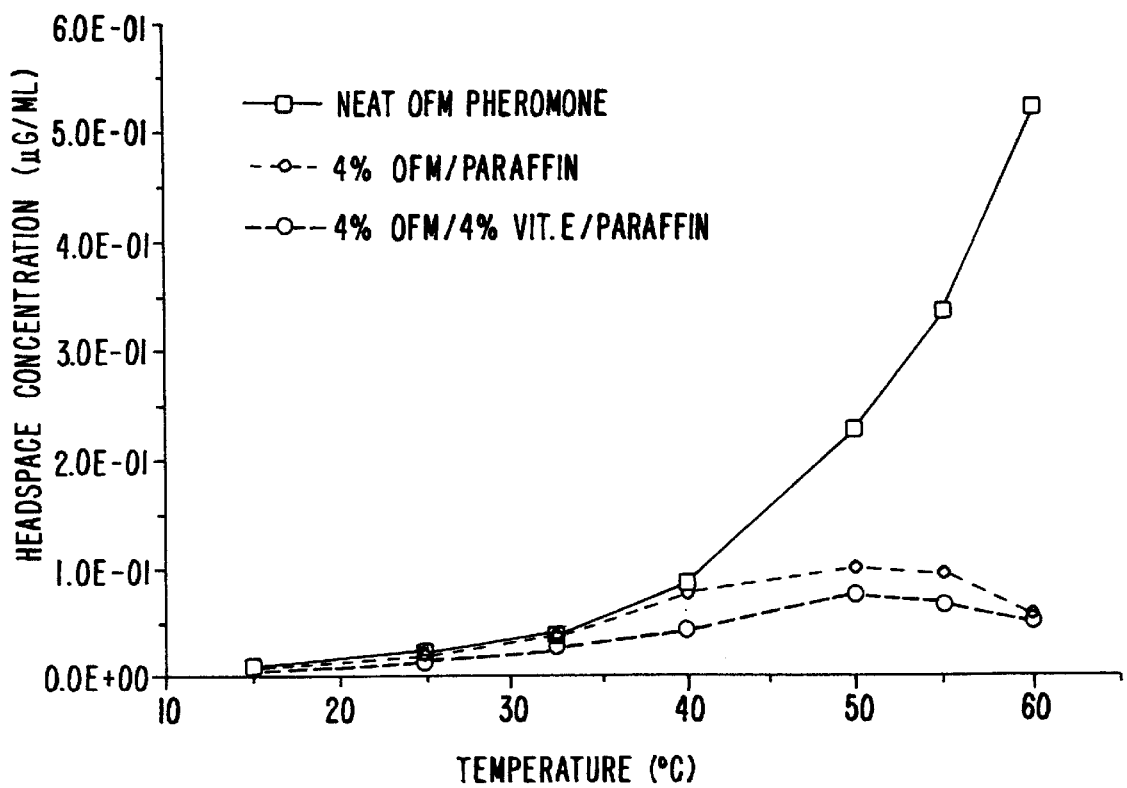
FIG. 8 is a graph illustrating equilibrium headspace concentrations of pheromone above mixtures of pheromone, paraffin and vitamin E.
Figure 9:
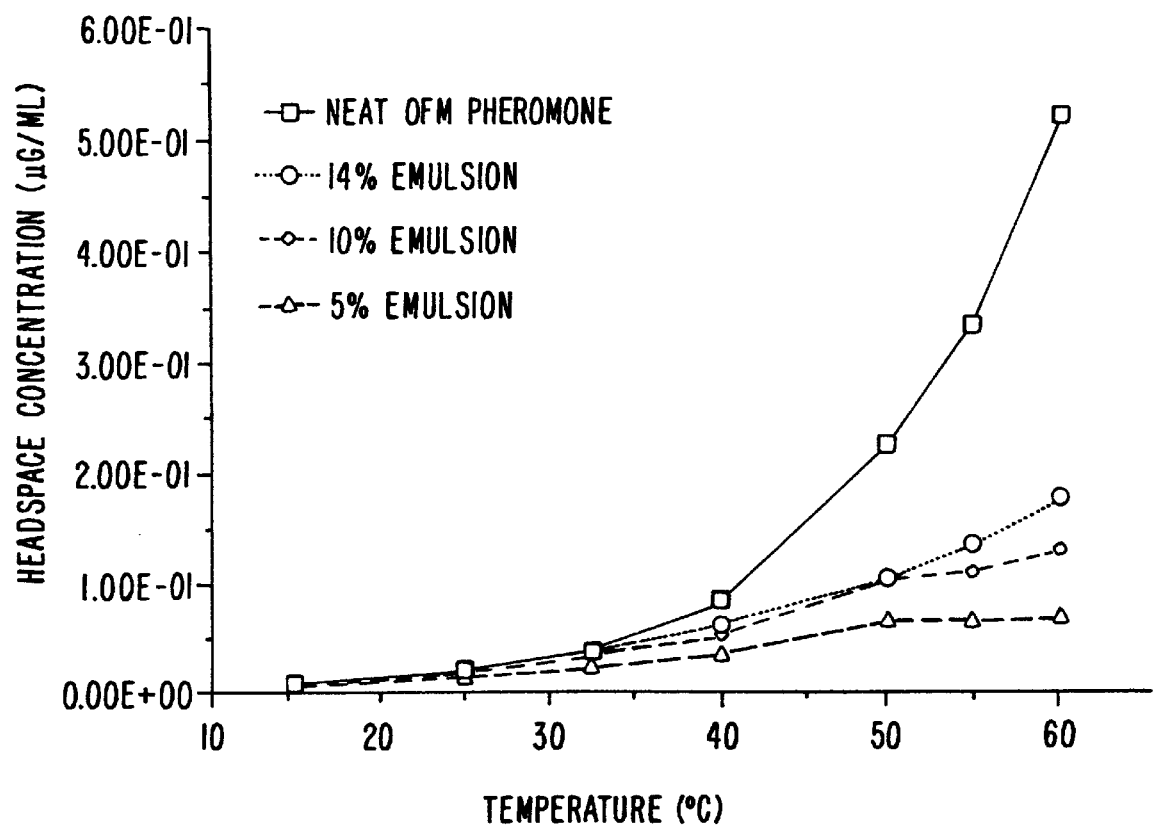
FIG. 9 is a graph illustrating equilibrium headspace concentrations of pheromone above paraffin emulsions.

The graphs in FIGS. 8 and 9 show the concentration of pheromone in a 1 ml sample of the headspace at temperatures ranging from 15° C. to 60° C. The calculated partition coefficients are shown in the graphs in FIGS. 10 and 11.

FIG. 8 shows the OFM pheromone headspace concentrations above samples of pheromone mixed with paraffin and vitamin E. The FIG. 8 shows that the vitamin E acts as a volatility suppressant, reducing the tendency of pheromone to move from the wax into the air headspace above the wax. The headspace concentration for neat pheromone increased exponentially with temperature. When the melting temperature of the paraffin was reached (approximately 50° C.), the headspace concentration of the pheromone actually decreased, indicating that the solubility of pheromone in molten paraffin was greater than in solid paraffin. FIG. 8 also shows that vitamin E affects the solubility of the pheromone in the wax, thus affecting the release rate. When vitamin E was added to the mixture of pheromone and paraffin, there was a further decrease in the headspace concentration of pheromone, indicating that the addition of vitamin E to the paraffin increased the solubility of the pheromone in the wax matrix.

FIG. 9 shows equilibrium OFM pheromone headspace concentrations above samples of pheromone dispersed in paraffin emulsions. The headspace concentration for neat pheromone increased exponentially with temperature. When the pheromone was mixed in a paraffin emulsion, there was a decrease in the headspace concentration, especially at the higher temperatures. When the melting temperature of the paraffin was reached, the headspace concentration of the pheromone leveled off for the lowest concentration of pheromone, 5% of the dry weight basis, indicating that the solubility of pheromone in the molten paraffin mixture was greater than in the solid paraffin mixture. For the next higher concentration of pheromone, 10% on a dry weight basis, the headspace concentration leveled off briefly, then began increasing at 60° C. For the highest pheromone concentration, 14% of a dry weight basis, the headspace concentration increased with temperature along the entire range of temperatures tested, but was considerably lower than neat pheromone. These results indicate that the pheromone is soluble in paraffin emulsions, but the emulsions may become saturated at high pheromone concentrations.

Figure 10:
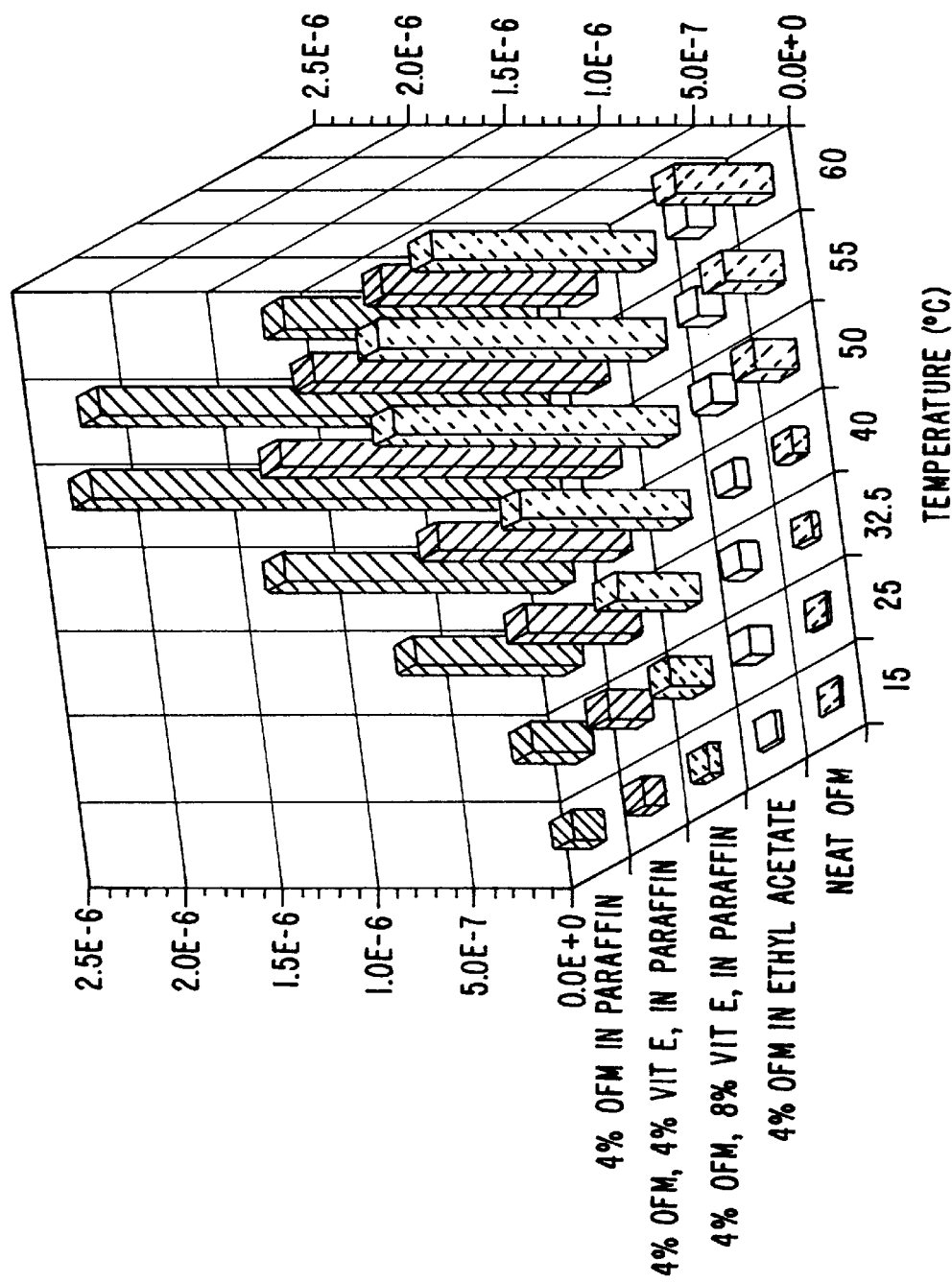
FIG. 10 is a graph illustrating air/wax partition coefficients for pheromone in mixtures of paraffin and vitamin E.

FIG. 10 shows the air/wax partition coefficients for OFM pheromone in mixtures of paraffin and vitamin E, calculated for the results shown in FIG. 8. The partition coefficients indicate the ratio of headspace concentration to concentration in the sample, and provide insight into the tendency of the pheromone to escape from the carrier into the air. For all the mixtures of pheromone in paraffin, the partition coefficients increased with temperature until the melting point of the wax was reached at 50° C. Above that temperature, the partition coefficients began to decrease. Also, the partition coefficients decreased at all temperatures when vitamin E was added to the paraffin, with a greater decrease seen in the presence of a greater amount of vitamin E. It seems that the solubility of the pheromone in the paraffin matrix increased when vitamin E was added. The partition coefficients for OFM pheromone in ethyl acetate were relatively low, indicating a greater solubility of the pheromone in this solvent. Pheromone is more likely to escape (partition) into the headspace when its solubility in the carrier is low. In contrast, the partition coefficients for neat pheromone increased at each temperature. For neat pheromone, the actual headspace concentration was greater, but dividing the headspace concentration by 100% resulted in a lower ratio than that obtained when dividing by the pheromone concentration in the mixtures.

Figure 11:
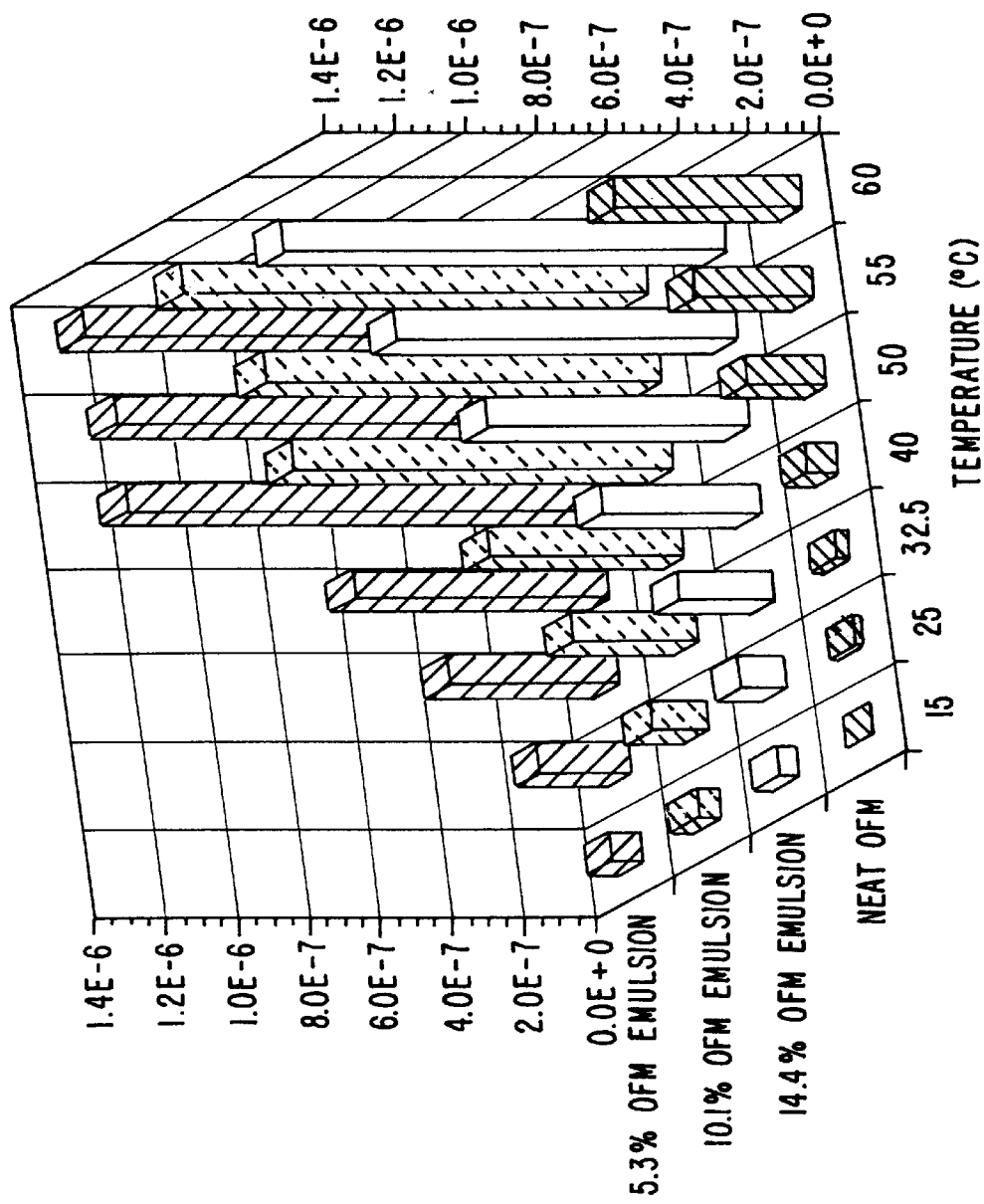
FIG. 11 is a graph illustrating air/wax partition coefficients for pheromone in paraffin emulsions.

FIG. 11 shows the air/wax partition coefficients for OFM pheromone in paraffin emulsions. The trends are similar to those in FIG. 10. For the pheromone in paraffin emulsions, the partition coefficient increases with temperature, although the partition coefficient levels out at the melting temperature of the paraffin for the lower pheromone concentrations. The partition coefficients decrease when the concentration of pheromone in the emulsion increases, because of the division by larger percentages. The results indicate that the solubility is increasing in mixtures with greater concentrations of pheromone. The partition coefficients for the pheromone in paraffin emulsions are on the same order of magnitude as the partition coefficients for mixtures of pheromone in paraffin and vitamin E. With a constant pheromone concentration, a higher partition coefficient indicates a higher release rate.

Determination of controlled release of the pheromone, expressed as the partition coefficient is a quick way of determining relative release rates for pheromone in different formulations.

Figure 12:
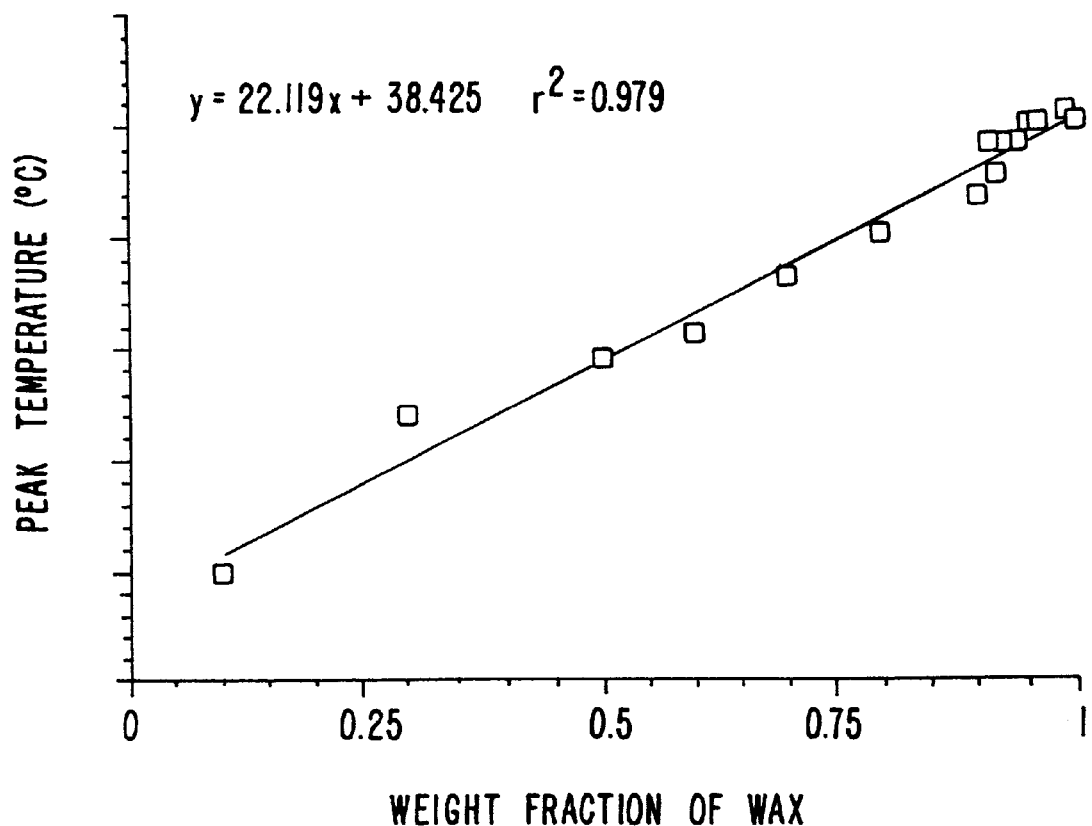
FIG. 12 is a phase diagram of paraffin wax/pheromone mixtures, constructed from peak melting temperatures measured on a differential scanning calorimeter (DSC).

The results of the differential scanning calorimetry (DSC) experiments are shown in FIG. 12. In mixtures of OFM pheromone and paraffin wax, as the pheromone concentration is increased (i.e., the weight fraction of the wax decreased), the peak melting temperature of the wax is lowered. The pheromone does affect the melting behavior of the wax, and the results indicate that OFM pheromone is soluble in paraffin. These results are important because they indicate that the mechanism of pheromone release from paraffin is partition controlled, and that the solubility of the pheromone in the paraffin mixture affects the release rate. This shows that the release rate can be manipulated by changing the formulation, thus affecting the solubility and partition coefficients.

Figure 13:
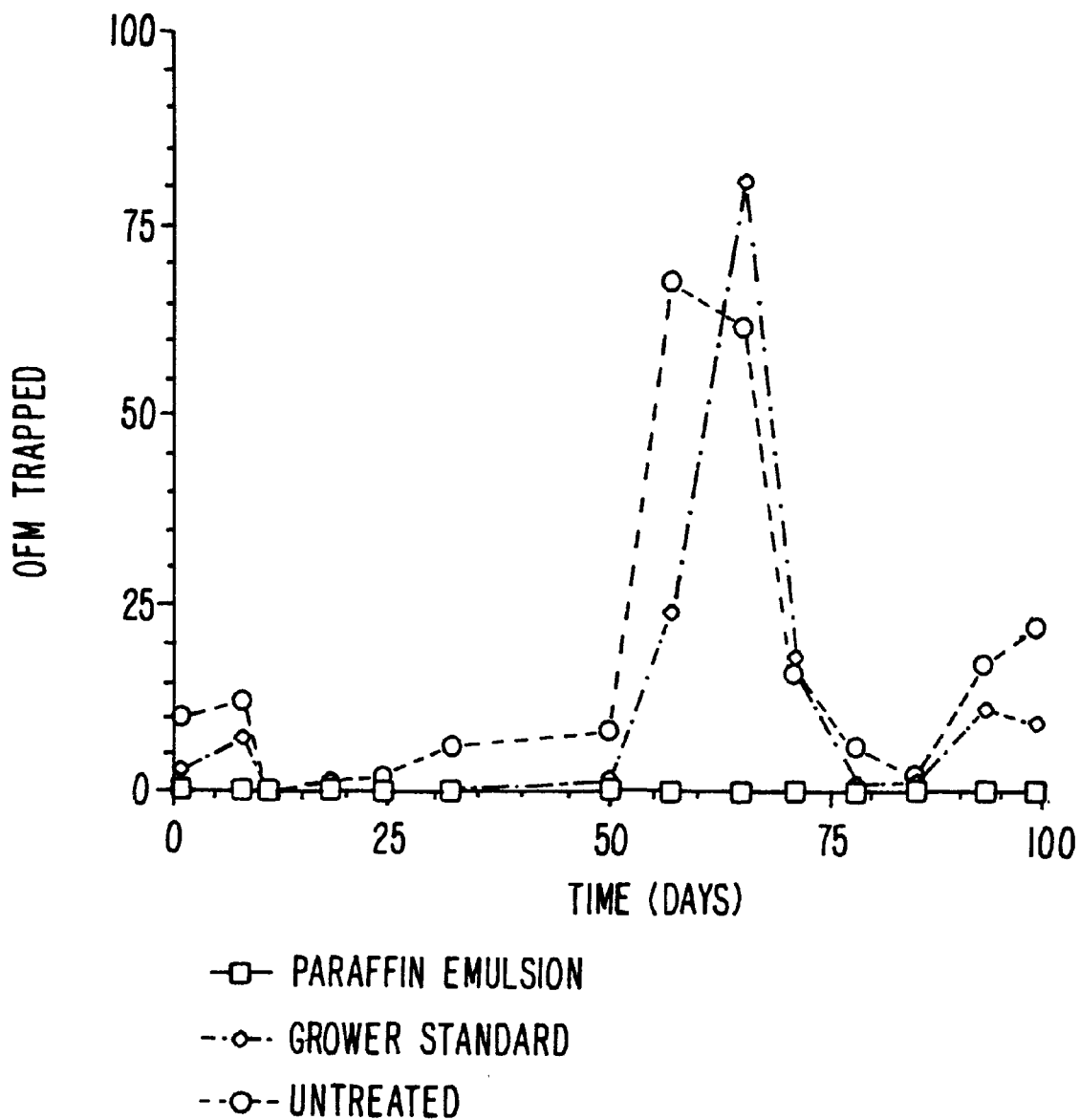
FIG. 13 is a graph showing the number of oriental fruit moths trapped in an untreated commercial peach block, in a block treated with the standard pesticide program, and a block treated with a pheromone paraffin emulsion.

The results of field trials in a commercial peach orchard in Marysville, Calif. are shown in FIG. 13 and in Table 1. FIG. 13 shows the OFM moths trapped in an untreated area of a commercial peach orchard, the number of moths trapped in another area of the same orchard which received a standard pesticide treatment in June, and a third area of the same orchard that was treated with the paraffin emulsion containing pheromone. For the period of the field trial, there was trap shut-down for OFM, indicating the pheromone release from the paraffin emulsion was sufficient to affect the behavior of the male insects. However, in late June, OFM shoot strikes were found in the paraffin treated blocks as well as the blocks treated with the commercial dispensers. For a period of approximately 4 months, moths were caught in the untreated areas of the orchard, whereas no moths were caught in the pheromone treated blocks. The amount of OFM pheromone released was sufficient to achieve trap shut-down for the period of the experiment. As indicated by the laboratory testing, illustrated in FIG. 7, such release can be substantially extended up to 500 days and perhaps even longer by a proper formulation design.

Because all the pheromone blocks were sprayed, a statistical comparison of the different treatments was made by comparing shoot strike damage. Twenty trees from each treatment block were randomly chosen and evaluated for shoot strike damage. The average number of twig strikes per tree for each treatment was calculated, and the results are shown in Table 1.

TABLE 1

Average number of shoot strikes per tree in a
commercial peach.orchard in Marysville, CA.

| Treatment | Mean Shoot Strikes* |
|---|---|
| Pheromone Commercial Dispenser I | 45$^a$ |
| Untreated | 41$^a$ |
| Pheromone Commercial Dispenser II | 27$^b$ |
| Paraffin Emulsion | 19$^b$ |
| Grower Standard | 7$^c$ |

*N (number of trees sampled) = 20
Shoot strike means OFM larval infestation in new shoots.

Growers standard is the grower practice to use pesticides at appropriate times.

Values in the Table 1 marked with the same letter are not significantly different from each other at the 95% confidence level.

At a 95% confidence level, the paraffin emulsion treated block was significantly better than the untreated block, significantly better than the commercial pheromone dispenser I (Consep®), treated block, and not significantly different from the commercial pheromone dispenser II (Hercon®) treated block. These pheromone dispensers are commercially available.

In other field trials the OFM pheromone was applied directly to the bark in a paraffin emulsion using a forestry paint marking gun. In these OFM field trials, the paraffin emulsion was applied to blocks of peach, nectarine, plum, and almond trees twice during the season. Trap shut-down occurred for an extended period of time, and levels of fruit damage were comparable to the levels obtained with conventional pesticide treatments.

Both laboratory results and field trials have shown that OFM pheromone can be dissolved in paraffin and released slowly for an extended period of time. The pheromone release-rate depends on additives to the wax, pheromone concentration, temperature, and surface area. Neat OFM pheromone readily degrades when exposed to air and UV light.

The release-rate can be manipulated by changing one or more of the paraffin formulation factors, and the pheromone can be protected from degradation in the environment.

UTILITY

This invention is useful for crop protection by providing a means and a method for control and management of insect pests. Such control is achieved by delivering pheromones to the potentially infested areas to be protected from infestation by the specific insect species. The wax carrier covers and adheres to the sprayed surface. Consequent water evaporation results in an adherent dried coating from which the pheromone is continuously released above the threshold level in an amount which is about the same or above the level of pheromone naturally released by the female insect. The male insect is unable to locate the female in the whole treated area.

The major feature of this invention is sprayability and biodegradability of the pheromone/wax formulation according to the invention. The formulated material can be sprayed or squirted from ground level and thus applied higher in the tree than a worker could reach hanging conventional plastic dispensers.

The current method meets all criteria needed for successful insect pest control using pheromones. It allows controlled release of the target insects' sex pheromone at the appropriate time, at the location where the insect pest appears and in concentration which will prevent males from chemically locating females and thus inhibit their reproduction. The current method is fully competitive with available conventional methods of insect control.

The invention provides numerous additional unexpected advantages not previously described or available in insect pest control and management.

The biodegradable wax carriers, while effective carriers for delivery of pheromones, are themselves completely biologically inactive and are subsequently biodegraded without causing any residual environmental or safety hazard. These compositions are safe and non-phytotoxic and are thus suitable for spraying of fruit orchards and other crops.

Versatility allows a choice of time, concentration and release-rate of the pheromone. Pheromone is released by diffusion of the bioactive agent through the biodegradable carrier matrix, by partitioning of the pheromone between the carrier wax and the air surrounding the wax carrier, and by the erosion or biodegradation of the carrier material by various environmental conditions, causing exposure of the bioactive agent.

The composition has extended longevity and, therefore, there is no need for repetitive application of the pheromone. Because the biodegradable wax compositions are designed specifically for the intended purpose, there is a zero-order, continuous and constant-rate release of the pheromone which can be designed to last as long as necessary for crop protection.

A specific composition can be designed for a specific pheromone and for a specific purpose for which it is intended. For example, an average release-rate of about 1 mg/day is achieved for over 6 months when 650 mg pheromone is added to about 15 g paraffin wax containing 1.3 g vitamin E, with a surface area of 45.6 cm$^2$ and a thickness of 0.38 cm. A higher average release-rate is obtained when vitamin E is omitted from the formulation. These values are close to the release range of 2–3 mg/day which has been found to be effective for oriental fruit moth control. As discussed above and seen in the figures, the release rate is easily modified by viscosity, pheromone concentration, temperature, surface area, etc.

Additionally, the invention is economical in that the entrapment of the pheromone can be regulated such that the carrier is chosen to entrap the minimum amount of pheromone needed for crop protection. In this respect, paraffin carrier is the most preferred as it entraps 100% of the added pheromone.

The invention does not require any additional handling other than the original application. No removal of containers or washing of residues is necessary. Application does not require any special equipment. The best mode of practicing the invention is to spray the aqueous formulation or spread granules on the trees or plants. This can be achieved by using common types of agricultural sprayers or spreaders, or commercial grease pumps.

Possible modifications of the invention include microencapsulation of the pheromone, for example in liposomes before incorporation in the biodegradable wax. This would provide additional control of the release-rate of the bioactive compound.

The current invention does not include the use of synthetic polymers or other non-biodegradable materials. All of the materials used in the formation of the biodegradable materials coating according to the invention are biodegradable and edible too.

EXAMPLE 1

Sprayable or Solid, Biodegradable Paraffin Wax Carrier-Pheromone Composition This example describes preparation of the composition comprising aqueous emulsion of paraffin wax and pheromone. Before pheromone addition, the paraffin wax was investigated for phytotoxicity as described in Example 2.

Oriental fruit moth (OFM) pheromone obtained from Bedoukian Research Inc., Danbury, Conn., and vitamin E (mixed-tocopherols) obtained from Prime Natural Health Labs, Carson, Calif., were added into molten paraffin wax (Aldrich Chemical Co., Milwaukee, Wis.) and mixed by stirring on a hot plate. The molten mixture was then poured into molds that formed disks with a 7.6 cm (3 in) diameter, thickness of 4 mm (0.16 in), and surface area of 45.6 cm$^2$ (7.1 in$^2$). The disks were placed in a commercial almond orchard for mating disruption field trials.

Aqueous paraffin emulsions were prepared by mixing OFM pheromone, vitamin E, soy oil, and emulsifier (Span 60®), obtained from Sigma Chemical Co., St. Louis, Mo., into molten paraffin wax while stirring on a hot plate. Water heated to 70° C. was added to the wax mixture while stirring rapidly. The mixture was then emulsified using a hand mixer. The emulsions were approximately 30% wax, 4% pheromone, 60% water, and 6% soy oil, vitamin E and emulsifier.

EXAMPLE 2

Pheromone Release from Paraffin Carrier Measurements

This example describes procedures and experiments used for determination of pheromone release from paraffin carriers. The aim of these studies was to determine whether pheromone applied to a plant surface can be released for period longer than 6 weeks.

Laboratory tests were designed to measure the effects of formulation, temperature, pheromone concentration, and surface area on the pheromone release rate. Once the pheromone-containing paraffin disks and emulsions were prepared, they were placed in flow cells in an environmental chamber.

The flow cells were machined from aluminum with a 8 or 15 cm (4 or 6 in) diameter and a 5 cm (2 in) depth. An aluminum lid was bolted to the top of each flow cell and sealed with a Teflon gasket. Each cell had a flow meter mounted at the inlet and was placed in an oven maintained at 32° C. (90° F.) during the experiment. A 0.5 L/minute air stream entered the flow cells and was distributed over the surface of the carrier material after passing through a metal diffusing screen. The released pheromone was trapped in a porous polymer absorbent (Super Q), obtained from Alltech, Deerfield, Ill., contained in glass tubes at the exit port located near the bottom of each cell. Periodically, the pheromone was eluted from the adsorbent using ethanol.

Synthetic OFM pheromone is a mixture of 3 components, (Z)-8-dodecenyl acetate, (E)-8-dodecenyl acetate, and (Z)-8-dodecenol, in a 93:6:1 ratio. The amount of pheromone in the sample captured from the air stream which was periodically eluted from the traps with ethanol, was measured using a gas chromatograph (GC) (Hewlett Packard Model 5890, Palo Alto, Calif.) equipped with a flame ionization detector and a 30 m capillary column obtained from DB-1, J&W Scientific, Folsom, Calif. Methyl tridecanoate commercially available from Aldrich Chemical Co., Milwaukee, Wis., was used as an internal standard to quantify the amount of pheromone present in the samples.

EXAMPLE 3

Measurements of the Pheromone Release in Laboratory Conditions

This example describes studies performed in the laboratory setting designed to measure the pheromone release-rate from paraffin carriers.

Laboratory experiments were designed to measure the pheromone release-rate from various carrier materials, the effect of additives to the formulation, and the effect of environmental variables. Various materials containing pheromone were placed in the flow cells and the release-rate was monitored by periodically eluting the pheromone and measuring its quantity by gas chromatography.

In one experiment, the release-rate of 650 mg OFM pheromone from a 15 g paraffin disk containing 1.3 g vitamin E was measured.

In another experiment, the release-rates for samples with and without vitamin E were compared. Each 15 g paraffin disk contained 480 mg pheromone; and one sample contained 1.3 g vitamin E added to the mixture.

In a third experiment, the pheromone and 1.4 g vitamin E were added to 15 g samples of a commercial fruit wax (EFW-1) obtained from, Knapp Manufacturing Co., Fresno, Calif. The fruit wax emulsions contained 35% solids.

Once the pheromone containing paraffin disks and emulsions were prepared, they were placed in flow cells in the oven with an air stream passing over the surface. By periodically eluting the traps and using the GC to quantify the mass of pheromone released, the average release-rate was calculated. The effects of formulation variables were tested in this manner.

Tests were also conducted to determine the extent of pheromone degradation that might occur under field conditions when the pheromone is exposed to ultraviolet (UV) light and oxygen. Five pheromone mixture samples were placed in petri dishes on the roof of a 4-story building in August at the UC Davis campus. One sample consisted of 650 mg OFM pheromone in 15 g paraffin wax with no vitamin E. Three samples consisted of 650 mg OFM pheromone in 15 g paraffin wax with 3 different levels (1300, 650 and 65 mg) of vitamin E. A final sample consisted of neat OFM pheromone. Fractions of the samples were removed periodically, analyzed on the GC, and their degradation was determined.

For samples in which the pheromone was dissolved in paraffin wax, the pheromone was extracted from the wax using solvents. The wax/pheromone sample was first dissolved in chloroform. Most of the chloroform was evaporated, then cold acetonitrile was added to the mixture to precipitate the wax and leave the pheromone dissolved. The mixture was filtered through filter paper to remove the wax, then the acetonitrile was evaporated and replaced with ethanol. The extracted pheromone was then analyzed on a GC. Oxidative or UV degradation of the pheromone was indicated by the presence of additional peaks on the gas chromatogram. Samples containing degradation peaks on the gas chromatogram could be further analyzed on a gas chromatograph-mass spectrometer (GC-MS) for identification of the degradation products.

EXAMPLE 4

Headspace Analysis

This example describes procedures used to analyze release of pheromone into a headspace.

Samples of paraffin mixtures containing OFM pheromone were placed in 10 ml headspace vials and sealed. The headspace vials were brought to temperatures ranging from 15 to 60° C., allowed to reach equilibrium, and the air (headspace) above the sample was analyzed on a GC. Samples (1 ml) of the headspace were withdrawn from the vials and injected on the GC. Because of the relatively large sample size, a cryofocusing technique was used. With this technique, the first loop of the GC capillary column was immersed in liquid nitrogen to condense the pheromone and focus the peak. The 1 ml volume of headspace removed for each analysis was replaced with 1 ml of air to maintain a constant air pressure in the vial. Each sample was analyzed a minimum of three times, and the values were averaged. This procedure was repeated at each temperature within the range tested. To obtain partition coefficients for the various paraffin mixtures, the headspace concentration was divided by the concentration of pheromone in the paraffin mixture placed in the vial.

EXAMPLE 5

Differential Scanning Calorimetry Analysis

This example describes differential scanning calorimetry (DSC) analyses of pheromone compositions in paraffin.

Samples of paraffin containing different proportions of OFM pheromone were placed in small aluminum pans and sealed. The samples were analyzed using a differential scanning calorimeter (DSC) (Perkin-Elmer, Norwalk, Conn.), scanning from 0 to 77° C. at a scan speed of 10° C./min. The DSC plots were analyzed for peak melting temperature, and comparisons were made among the different pheromone/paraffin compositions.

EXAMPLE 6

Field Studies for Determination of Pheromone Release from Paraffin Disks

This example describes the actual field tests studying the release of the pheromone from paraffin disks in a commercial almond orchard.

Field tests were performed by placing the pheromone/paraffin disks on branches in a commercial almond orchard. Five trees in a diamond shaped grid pattern were treated with 15 g paraffin disks containing 650 mg OFM pheromone and 1.3 g vitamin E. The disks were attached to branches at a height of 6 ft, and one disk was applied per tree. An OFM pheromone monitoring trap obtained from Pherocon 1C, Trece, Salinas, Calif., was placed in the center tree at a height of 6 ft. The field tests were run in quadruplicate. As a control, 4 pheromone monitoring traps were placed in an untreated area of the orchard, 30 rows upwind, so the trap counts would not be affected by the pheromone being released from the treated blocks in the orchard. The number of insects trapped in the treated and untreated blocks of the orchard were counted periodically throughout the entire season.

Because of the encouraging results obtained by placing the pheromone/paraffin disks and monitoring traps at 6 ft in the trees, a question was raised regarding the vertical distribution of pheromone and moths in the tree canopy. Therefore, OFM monitoring traps were attached to 20 ft polyvinyl chloride (PVC) pipes at heights of 1.8, 3.7, and 5.5 m (6, 12, and 18 ft), and placed in treated and untreated almond trees. As before, five trees in a diamond shaped grid pattern were treated with 15 paraffin disks containing 650 mg OFM pheromone and 1.3 g vitamin E. Again, the treated trees were 30 rows downwind from the untreated trees. The paraffin disks were attached to the tree trunk at a height of 6 ft, and one disk was applied per tree. An OFM pheromone monitoring trap was placed in the center tree at a height of 6 ft. In this experiment, the field tests were run in triplicate. Also, 3 blocks of trees were treated with commercial OFM plastic pheromone dispensers (Pacific Biocontrol, Davis, Calif.).

EXAMPLE 7

Sprayable, Biodegradable Paraffin Pheromone Carrier

This example illustrates preparation of an aqueous paraffin emulsion, suitable as a carrier for pheromones.

Basic Paraffin Emulsion 100 g of paraffin is melted. Then 150 g of heated water and 1-10 g of emulsifier are added to the paraffin. The amount of emulsifier ranges from about 1 to 10 g, depending on the specific emulsifier. Emulsifiers used include lecithin, mono- and diglycerides, sorbitan monopalmitate, sorbitan monooleate and sorbitan monostearate. The pheromone, antioxidant, ultraviolet blocker, volatility suppressant, and any other additives are then added to the paraffin emulsion. After the emulsion is mixed well, then the mixture is mechanically emulsified using a high-speed mixer. The paraffin emulsion is sprayed on the treated trees, plant or soil or molded to paraffin blocks as in Example 10.

Paraffin-Pheromone Emulsion (A)

Emulsion A comprises the basic paraffin emulsion containing about 4 g of oriental fruit moth pheromone was added and stirred in the paraffin mixture.

Paraffin-Pheromone-Vitamin E Emulsion (B)

Emulsion B was prepared essentially as emulsion A. Additionally, solution B contained up to approximately 8 g of vitamin E added to the paraffin emulsion.

Paraffin-Pheromone-Emulsion Containing Antidegradative Additive (C)

Emulsion C is prepared essentially the same as emulsion A. Additionally, emulsion C contains approximately 150 mg of β-carotene.

Paraffin-Pheromone Emulsion Containing Antibacterial and Antidegradative Additive (D)

Emulsion D is prepared essentially the same as emulsion A. Additionally, emulsion D contains about 0.1 g of potassium sorbate providing antimicrobial protection, and B-carotene added in 0.1 g within this solution provided protection against ultraviolet degradation.

EXAMPLE 8

Sprayable, Biodegradable Wax/Pheromone Carrier

This example illustrates preparation of wax aqueous emulsions, other than paraffin, suitable as a carrier for pheromones.

Beeswax, lanolin, shellac wax, candilla wax, carnauba wax, bayberry wax, sugar cane wax, paraffin, micrystalline, ozocerite, ceresin, montan, or their combination were formulated in the same manner as the aqueous paraffin emulsion described in Example 8.

EXAMPLE 9

Solid Biodegradable Paraffin Pheromone Carrier

This example illustrates preparation of a solid paraffin wax carrier material that has been pre-formed into shapes, sizes and thicknesses necessary to provide the desired release-rate. The solid material is suitable as a carrier for pheromones and other bioactive materials.

Solid Paraffin Disks 100 g of paraffin is heated to melt the paraffin and 1–5 g of pheromone was added. The pheromone, antioxidant, ultraviolet blocker, volatility suppressant, and any other additives are then added to the molten paraffin and mixed. The mixture is then molded into solids with the desired shape, size and thickness.

Solid Wax Disks

Solid wax disks of beeswax, candelilla wax, carnauba wax or fruit wax are formulated in the same manner as solid paraffin disks.

EXAMPLE 10

Field Trials of Paraffin/Pheromone Aqueous Emulsions

This example illustrates specific field trials performed for the determination of release of pheromone from paraffin carrier disks or sprays.

Field tests were performed in the commercial peach orchard by applying 7.5 g of a paraffin emulsion containing 4% OFM pheromone, 4% soy oil, 1% vitamin E and 2% Span 60 to scaffold limbs in a 5 acre block of commercial peach trees in early March. The emulsion had a consistency similar to toothpaste, was applied to the trees using a hand grease gun, at a rate of 30–35 g pheromone per acre. Four OFM pheromone monitoring traps (Pherocon 1C, Trece, Salinas, Calif.) were placed in the pheromone emulsion treated block. As a control, 4 pheromone monitoring traps were placed in an untreated area of the orchard and 4 traps in a standard treated area. The number of insects trapped in the treated and untreated blocks were counted periodically throughout the season.

In the same orchard, four 5-acre blocks of trees were also treated with commercial OFM mating disruption plastic pheromone dispensers (Consep Inc., Bend, OR and Hercon, Emigsville, Pa.). There were two 5-acre blocks treated with Consep® dispensers and two 5-acre blocks treated with Hercon® dispensers. The commercial dispensers were applied in early March, and again in early June. Results are seen in Table 1.

A less viscous paraffin emulsion containing OFM pheromone was prepared for another field trial. The emulsion was prepared by the procedure described above, but a smaller amount of emulsifier was used (about 1%), resulting in a less viscous emulsion. The emulsion was applied to two-acre blocks of peaches, nectarines, plums, and almonds using a forestry paint marking gun, applying 4 g emulsion per tree and achieving an application rate of approximately 30 g pheromone per acre. Pheromone monitoring traps were placed in treated and untreated blocks in the various orchards.

EXAMPLE 11

Spray Delivery System

This example illustrates a manually operated spray delivery system for the invention.

A manually operated spray delivery system consists of a small reservoir tank for the pheromone carrier, pump, and spray gun. The system is used to apply relatively viscous fluids to the trunk, scaffold limbs, and upper canopy of the tree. The concentration of pheromone in the carrier and the quantity applied per orchard area is adjusted to match the amount now used in commercial plastic polymer dispensers. The fraction of carrier material actually deposited on each tree is determined by the laboratory testing.

Field evaluations using OFM pheromones are conducted in research orchards. Tests are conducted to determine the relative effect and duration of sprayed pheromones on OFM behavior.

The pheromone carrier was applied to four 5-tree groups within an untreated block. The potential for mating disruption is evaluated by placing sex pheromone traps in the center tree of each group and counting the number of males caught over time. The pheromone release-rate from the carrier material affects capture rates in the traps. Comparisons were made with counts from traps placed in untreated trees near the treated ones. The natural degradation of the pheromone carrier material was monitored over the growing season and into the dormancy period.

What is claimed is:

1. An aqueous emulsion comprising a pheromone dispersed and entrapped in a biodegradable wax carrier, the emulsion comprising:
   (a) the wax carrier in amount of at least about 10% by weight; and
   (b) the pheromone in amount from about 0.01% to about 20% by weight;
   wherein the emulsion is suitable for mating disruption of insects by releasing the pheromone from the wax carrier at a continuous and constant zero-order rate for about three weeks or more.

2. The emulsion of claim 1, wherein the wax carrier is present in amount from about 10% to about 40% by weight.

3. The emulsion of claim 1, wherein the emulsion contains from about 50% to about 90% by weight of water.

4. The emulsion of claim 1, the emulsion further containing one or more additives selected from the group consisting of lipids, emulsifiers, plasticizers, UV blockers and absorbers, antimicrobials, antioxidants, and volatility suppressants.

5. The emulsion of claim 4, wherein the additive is present in amount from about 0.001% to about 20% by weight.

6. The emulsion of claim 4, wherein the additive is present in amount from about 1% to about 6% by weight.

7. The emulsion of claim 5, wherein the additive is an emulsifier selected from the group consisting of lipids, soy oil, lecithins, modified lecithins, monoglycerides, diglyceridies, sorbitans, and fatty acids, and combinations thereof.

8. The emulsion of claim 7, wherein the additive is the emulsifier added in amount from about 1% to about 6% by weight.

9. The emulsion of claim 4, wherein the additive is the antioxidant added in amount from about 0.1% to about 3% by weight.

10. The emulsion of claim 9, wherein the antioxidant is vitamin E, butylated hydroxyanisole, butylated hydroxytoluene, or other antioxidants.

11. The emulsion of claim 4, wherein the emulsion comprises about 60% by weight of water, about 30% by weight of the paraffin wax, about 4% by weight of the pheromone and about 6% by weight of emulsifiers, plasticizers, and antioxidants combined.

12. The emulsion of claim 1, wherein the emulsion comprises from about 30% to about 40% by weight of the wax carrier, from about 50% to about 90% by weight of water, from about 0.1% to about 10% by weight of the pheromone, and from about 1% to about 10% by weight of additives.

13. The emulsion of claim 1, wherein the wax carrier is selected from the group consisting of paraffin, carnauba wax, beeswax, candelilla wax, fruit wax, lanolin, shellac wax, bayberry wax, sugar cane wax, microcrystalline wax, ozocerite, ceresin, montan wax, and combinations thereof.

14. The emulsion of claim 12, wherein the wax carrier is paraffin.

15. The emulsion of claim 1, the emulsion further containing two or more different types of pheromones.

16. The emulsion of claim 1, the emulsion further containing an additional bioactive compound.

17. The emulsion of claim 1, wherein the emulsion is sprayable, squirtable or spreadable.

18. The emulsion of claim 17, wherein the emulsion is sprayable.

19. The emulsion of claim 1, the emulsion further containing liposomes which encapsulate the wax carrier.

20. The emulsion of claim 1, wherein the emulsion is suitable for mating disruption of insects by releasing the pheromone from the wax carrier at a continuous and constant zero-order rate for about six weeks or more.

21. The emulsion of claim 1, wherein the emulsion is suitable for mating disruption of insects by releasing the pheromone from the wax carrier at a continuous and constant zero-order rate for about two months or more.

22. An aqueous emulsion comprising a pheromone dispersed and entrapped in a biodegradable wax carrier, the emulsion produced by:

providing a heated wax carrier and an emulsifier;

adding the pheromone to the heated wax carrier; and adding water to produce the aqueous emulsion comprising at least about 10% by weight of the wax carrier and from about 0.01% to about 20% by weight of the pheromone;

wherein the emulsion is suitable for mating disruption of insects by releasing the pheromone from the wax carrier at a continuous and constant zero-order rate for about three weeks or more.

23. The emulsion of claim 22, wherein the wax carrier is selected from the group consisting of paraffin, carnauba wax, beeswax, candelilla wax, fruit wax, lanolin, shellac wax, bayberry wax, sugar cane wax, microcrystalline wax, ozocerite, ceresin, montan wax, and combinations thereof.

24. The emulsion of claim 22, wherein the paraffin is present in amount from about 10% to about 40% by weight, the pheromone is present in amount from about 0.1% to about 10% by weight, and water is present in amount from about 50% to about 90% by weight.

25. The emulsion of claim 22, the emulsion further containing one or more additives selected from the group consisting of lipids, plasticizers, UV blockers and absorbers, antimicrobials, antioxidants, and volatility suppressants.

26. The emulsion of claim 22, wherein the emulsion is suitable for mating disruption of insects by releasing the pheromone from the wax carrier at a continuous and constant zero-order rate for about six weeks or more.

27. The emulsion of claim 22, wherein the emulsion is suitable for mating disruption of insects by releasing the pheromone from the wax carrier at a continuous and constant zero-order rate for about two months or more.

28. A method of making an aqueous emulsion comprising a pheromone dispersed and entrapped in a biodegradable wax carrier, the method comprising:

providing a heated wax carrier and an emulsifier;

adding the pheromone;

adding water to produce the aqueous emulsion comprising at least about 10% by weight of the wax carrier and from about 0.01% to about 20% by weight of the pheromone;

wherein the emulsion is suitable for mating disruption of insects by releasing the pheromone from the wax carrier at a continuous and constant zero-order rate for about three weeks or more.

29. The method of claim 28, wherein the wax carrier is selected from the group consisting of paraffin, carnauba wax, beeswax, candelilla wax, fruit wax, lanolin, shellac wax, bayberry wax, sugar cane wax, microcrystalline wax, ozocerite, ceresin, montan wax, and combinations thereof.

30. The method of claim 28, wherein the pheromone is present in amount from about 10% to about 40% by weight, the pheromone is present in amount from about 0.1% to about 10% by weight, and water is present in amount from about 50% to about 90% by weight.

31. The method of claim 28, wherein the emulsion is suitable for mating disruption of insects by releasing the pheromone from the wax carrier at a continuous and constant zero-order rate for about six weeks or more.

32. The method of claim 28, wherein the emulsion is suitable for mating disruption of insects by releasing the pheromone from the wax carrier at a continuous and constant zero-order rate for about two months or more.

33. A method for a controlled and continuous release of a pheromone from a wax carrier at a continuous and constant zero-order rate, the method comprising applying an effective amount of the aqueous emulsion of claim 1 over an area to be treated.

34. The method of claim 33, wherein the step of applying is spraying.

35. The method of claim 33, wherein the pheromone is applied at a rate of 30–35 grams of pheromone per acre.

36. The method of claim 33, wherein the pheromone is released about the same or above the level of pheromone naturally released by the female insect.

37. The method of claim 33, wherein the pheromone provides insect control during the mating season.

* * * * *